US011730199B2

(12) United States Patent
Atkins et al.

(10) Patent No.: US 11,730,199 B2
(45) Date of Patent: Aug. 22, 2023

(54) CARTRIDGES FOR VAPORIZER DEVICES

(71) Applicant: JUUL Labs, Inc., San Francisco, CA (US)

(72) Inventors: Ariel Atkins, San Francisco, CA (US); Adam Bowen, San Mateo, CA (US); Steven Christensen, San Mateo, CA (US); Esteban Leon Duque, San Francisco, CA (US); James Monsees, San Francisco, CA (US)

(73) Assignee: JUUL Labs, Inc., Washington, DC (US)

(*) Notice: Subject to any disclaimer, the term of this patent is extended or adjusted under 35 U.S.C. 154(b) by 905 days.

(21) Appl. No.: 16/435,162

(22) Filed: Jun. 7, 2019

(65) Prior Publication Data

US 2019/0373953 A1 Dec. 12, 2019

Related U.S. Application Data

(60) Provisional application No. 62/848,681, filed on May 16, 2019, provisional application No. 62/682,144, filed on Jun. 7, 2018.

(51) Int. Cl.
| | |
|---|---|
| *A24F 40/46* | (2020.01) |
| *A24F 40/44* | (2020.01) |
| *A24F 40/10* | (2020.01) |
| *A61M 11/04* | (2006.01) |
| *A61M 15/06* | (2006.01) |
| *A24F 40/485* | (2020.01) |
| *A61M 15/00* | (2006.01) |

(52) U.S. Cl.
CPC .............. *A24F 40/46* (2020.01); *A24F 40/44* (2020.01); *A24F 40/485* (2020.01); *A24F 40/10* (2020.01); *A61M 15/0001* (2014.02)

(58) Field of Classification Search
CPC .......... A24F 40/42; A24F 40/10; A24F 40/20; A24F 40/40; A24F 40/485
See application file for complete search history.

(56) References Cited

U.S. PATENT DOCUMENTS

| | | |
|---|---|---|
| 4,571,485 A | 2/1986 | Spector |
| 4,793,365 A | 12/1988 | Sensabaugh et al. |
| 4,819,665 A | 4/1989 | Roberts et al. |
| 4,947,874 A | 8/1990 | Brooks et al. |
| 4,947,875 A | 8/1990 | Brooks et al. |
| 5,042,509 A | 8/1991 | Banerjee et al. |
| 5,175,791 A | 12/1992 | Muderlak et al. |
| 5,183,062 A | 2/1993 | Clearman et al. |
| 6,471,782 B1 | 10/2002 | Fang et al. |
| 7,726,320 B2 | 6/2010 | Robinson et al. |
| 8,251,060 B2 | 8/2012 | White et al. |
| 8,387,612 B2 | 3/2013 | Damani et al. |

(Continued)

FOREIGN PATENT DOCUMENTS

| | | |
|---|---|---|
| CN | 102264420 B | 3/2014 |
| CN | 104544567 A | 4/2015 |

(Continued)

*Primary Examiner* — Alex B Efta
(74) *Attorney, Agent, or Firm* — Mintz Levin Cohn Ferris Glovsky and Popeo, P.C.

(57) ABSTRACT

Cartridges for use in vaporizer or vaporization devices are disclosed herein. Vaporizer or vaporization devices, atomizer components, and methods are also disclosed herein.

17 Claims, 23 Drawing Sheets

(56) References Cited

U.S. PATENT DOCUMENTS

| | | |
|---|---|---|
| 8,402,976 B2 | 3/2013 | Fernando et al. |
| 8,794,231 B2 | 8/2014 | Thorens et al. |
| 8,881,737 B2 | 11/2014 | Collett et al. |
| 8,991,402 B2 | 3/2015 | Bowen et al. |
| 9,016,274 B1 | 4/2015 | White |
| 9,055,617 B2 | 6/2015 | Thorens et al. |
| 9,078,473 B2 | 7/2015 | Worm et al. |
| 9,220,302 B2 | 12/2015 | Depiano et al. |
| 9,277,770 B2 | 3/2016 | Depiano et al. |
| 9,282,773 B2 | 3/2016 | Greim et al. |
| 9,364,800 B2 | 6/2016 | Dubief |
| 9,399,110 B2 | 7/2016 | Goodman et al. |
| 9,420,829 B2 | 8/2016 | Thorens et al. |
| 9,532,601 B2 | 1/2017 | Liu |
| 9,603,389 B2 | 3/2017 | Chen |
| 9,609,893 B2 | 4/2017 | Novak et al. |
| 9,674,894 B2 | 6/2017 | Schneider et al. |
| 9,687,027 B2 | 6/2017 | Poston et al. |
| 9,717,277 B2 | 8/2017 | Mironov |
| 9,814,263 B2 | 11/2017 | Cochand et al. |
| 9,844,234 B2 | 12/2017 | Thorens et al. |
| 9,861,139 B2 | 1/2018 | Boldrini |
| 9,913,493 B2 | 3/2018 | Worm et al. |
| 9,999,250 B2 | 6/2018 | Minskoff et al. |
| 10,015,990 B2 | 7/2018 | Mironov |
| 10,045,561 B2 | 8/2018 | Flick |
| 10,104,914 B2 | 10/2018 | Force |
| 10,143,233 B2 | 12/2018 | Dubief et al. |
| 10,194,693 B2 | 2/2019 | Wensley et al. |
| 10,206,429 B2 | 2/2019 | Davis et al. |
| 10,272,170 B2 | 4/2019 | Dubief |
| 10,299,514 B2 | 5/2019 | Bilat et al. |
| 10,327,475 B2 | 6/2019 | Silvestrini |
| 10,405,579 B2 | 9/2019 | Collett et al. |
| 2005/0019026 A1 | 1/2005 | Wang et al. |
| 2005/0034723 A1 | 2/2005 | Bennett et al. |
| 2005/0285538 A1 | 12/2005 | Jaworski et al. |
| 2007/0079889 A1 | 4/2007 | Lindsay et al. |
| 2007/0215168 A1 | 9/2007 | Banerjee et al. |
| 2008/0038363 A1 | 2/2008 | Zaffaroni et al. |
| 2008/0216828 A1 | 9/2008 | Wensley et al. |
| 2009/0230117 A1 | 9/2009 | Fernando et al. |
| 2009/0302019 A1 | 12/2009 | Selenski et al. |
| 2010/0181387 A1 | 7/2010 | Zaffaroni et al. |
| 2010/0186757 A1 | 7/2010 | Crooks et al. |
| 2011/0041861 A1 | 2/2011 | Sebastian et al. |
| 2012/0230659 A1 | 9/2012 | Goodman et al. |
| 2012/0312313 A1 | 12/2012 | Frija |
| 2013/0160765 A1* | 6/2013 | Liu .................. A24F 40/42 128/202.21 |
| 2013/0174842 A1 | 7/2013 | Young et al. |
| 2013/0255702 A1 | 10/2013 | Griffith et al. |
| 2013/0306064 A1 | 11/2013 | Thorens et al. |
| 2013/0319435 A1 | 12/2013 | Flick |
| 2014/0041658 A1 | 2/2014 | Goodman et al. |
| 2014/0096782 A1 | 4/2014 | Ampolini et al. |
| 2014/0109921 A1 | 4/2014 | Chen |
| 2014/0130816 A1* | 5/2014 | Liu .................. A24F 40/46 131/329 |
| 2014/0158129 A1 | 6/2014 | Pratt et al. |
| 2014/0261486 A1 | 9/2014 | Potter et al. |
| 2014/0261487 A1 | 9/2014 | Chapman et al. |
| 2014/0270729 A1 | 9/2014 | Depiano et al. |
| 2014/0301721 A1 | 10/2014 | Ruscio et al. |
| 2014/0334804 A1* | 11/2014 | Choi .................. A24F 40/60 392/404 |
| 2014/0353856 A1 | 12/2014 | Dubief |
| 2015/0059780 A1 | 3/2015 | Davis et al. |
| 2015/0090279 A1* | 4/2015 | Chen .................. A24F 40/44 131/329 |
| 2015/0125136 A1 | 5/2015 | Sanchez |
| 2015/0216237 A1 | 8/2015 | Wensley et al. |
| 2015/0223522 A1 | 8/2015 | Ampolini et al. |
| 2015/0223523 A1 | 8/2015 | Mccullough |
| 2015/0245659 A1 | 9/2015 | Depiano et al. |
| 2015/0282525 A1 | 10/2015 | Plojoux et al. |
| 2015/0335070 A1 | 11/2015 | Sears et al. |
| 2016/0007653 A1 | 1/2016 | Tu |
| 2016/0021933 A1 | 1/2016 | Thorens et al. |
| 2016/0044963 A1 | 2/2016 | Saleem |
| 2016/0088874 A1 | 3/2016 | Lipowicz |
| 2016/0143362 A1 | 5/2016 | Boldrini |
| 2016/0144458 A1 | 5/2016 | Boldrini |
| 2016/0150824 A1 | 6/2016 | Memari et al. |
| 2016/0174613 A1 | 6/2016 | Zuber et al. |
| 2016/0198770 A1 | 7/2016 | Alarcon |
| 2016/0262453 A1 | 9/2016 | Ampolini et al. |
| 2016/0262454 A1 | 9/2016 | Sears et al. |
| 2016/0286865 A1 | 10/2016 | King et al. |
| 2016/0309785 A1 | 10/2016 | Holtz |
| 2016/0309786 A1 | 10/2016 | Holtz et al. |
| 2016/0338407 A1 | 11/2016 | Kerdemelidis |
| 2016/0338408 A1 | 11/2016 | Guenther et al. |
| 2016/0338410 A1 | 11/2016 | Batista et al. |
| 2016/0345630 A1 | 12/2016 | Mironov et al. |
| 2016/0353801 A1* | 12/2016 | Zinovik .................. B32B 3/266 |
| 2017/0006916 A1* | 1/2017 | Liu .................. H05B 3/03 |
| 2017/0027226 A1 | 2/2017 | Mironov et al. |
| 2017/0027233 A1 | 2/2017 | Mironov |
| 2017/0027234 A1 | 2/2017 | Farine et al. |
| 2017/0035109 A1 | 2/2017 | Liu |
| 2017/0035112 A1 | 2/2017 | Thorens |
| 2017/0035113 A1 | 2/2017 | Thorens |
| 2017/0042243 A1 | 2/2017 | Plojoux et al. |
| 2017/0049154 A1 | 2/2017 | Batista |
| 2017/0065000 A1 | 3/2017 | Sears et al. |
| 2017/0079330 A1 | 3/2017 | Mironov et al. |
| 2017/0079332 A1 | 3/2017 | Li et al. |
| 2017/0086501 A1 | 3/2017 | Buehler et al. |
| 2017/0095000 A1 | 4/2017 | Spirito et al. |
| 2017/0105452 A1 | 4/2017 | Mironov et al. |
| 2017/0105454 A1 | 4/2017 | Li et al. |
| 2017/0108210 A1 | 4/2017 | Meinhart et al. |
| 2017/0112196 A1 | 4/2017 | Sur et al. |
| 2017/0119054 A1 | 5/2017 | Zinovik et al. |
| 2017/0127722 A1 | 5/2017 | Davis et al. |
| 2017/0135406 A1 | 5/2017 | Reevell |
| 2017/0143041 A1 | 5/2017 | Batista et al. |
| 2017/0144827 A1 | 5/2017 | Batista |
| 2017/0150755 A1 | 6/2017 | Batista |
| 2017/0164657 A1 | 6/2017 | Batista |
| 2017/0172208 A1 | 6/2017 | Mironov |
| 2017/0172212 A1 | 6/2017 | Phillips et al. |
| 2017/0188626 A1 | 7/2017 | Davis et al. |
| 2017/0196268 A1 | 7/2017 | Reevell |
| 2017/0196269 A1 | 7/2017 | Bernauer et al. |
| 2017/0202266 A1 | 7/2017 | Sur |
| 2017/0231276 A1 | 8/2017 | Mironov et al. |
| 2017/0231277 A1 | 8/2017 | Mironov et al. |
| 2017/0231278 A1 | 8/2017 | Mironov et al. |
| 2017/0245551 A1 | 8/2017 | Reevell |
| 2017/0273355 A1 | 9/2017 | Rogers et al. |
| 2017/0273360 A1 | 9/2017 | Brinkley et al. |
| 2017/0280771 A1 | 10/2017 | Courbat et al. |
| 2017/0280775 A1 | 10/2017 | Manca et al. |
| 2017/0280776 A1 | 10/2017 | Manca et al. |
| 2017/0280778 A1 | 10/2017 | Force |
| 2017/0325506 A1 | 11/2017 | Batista |
| 2017/0340018 A1 | 11/2017 | Thorens |
| 2017/0354184 A1 | 12/2017 | Mironov et al. |
| 2017/0360092 A1* | 12/2017 | Althorpe .................. F22B 1/284 |
| 2017/0360093 A1 | 12/2017 | Fernando |
| 2018/0007971 A1 | 1/2018 | Plojoux et al. |
| 2018/0014577 A1 | 1/2018 | Qiu |
| 2018/0020732 A1 | 1/2018 | Kozlowski et al. |
| 2018/0070641 A1 | 3/2018 | Batista et al. |
| 2018/0077967 A1 | 3/2018 | Hatton et al. |
| 2018/0080559 A1 | 3/2018 | Li et al. |
| 2018/0132528 A1 | 5/2018 | Sur et al. |
| 2018/0132532 A1* | 5/2018 | Batista .................. A24F 40/46 |
| 2018/0146711 A1 | 5/2018 | Mazur et al. |
| 2018/0153218 A1 | 6/2018 | Verleur et al. |
| 2018/0242642 A1 | 8/2018 | Silvesstrini et al. |
| 2018/0271140 A1 | 9/2018 | Kobal et al. |

(56) References Cited

U.S. PATENT DOCUMENTS

| | | |
|---|---|---|
| 2018/0303169 A1 | 10/2018 | Sears et al. |
| 2019/0045837 A1 | 2/2019 | Spencer |
| 2019/0166909 A1 | 6/2019 | Reevell |
| 2019/0166913 A1 | 6/2019 | Trzecieski |
| 2019/0200674 A1 | 7/2019 | Tucker et al. |
| 2019/0364968 A1 | 12/2019 | Fu et al. |
| 2020/0046033 A1 | 2/2020 | Robert et al. |
| 2020/0107572 A1 | 4/2020 | Marques et al. |
| 2020/0367569 A1 | 11/2020 | Farine |
| 2021/0204609 A1 | 7/2021 | Bilat et al. |

FOREIGN PATENT DOCUMENTS

| | | |
|---|---|---|
| CN | 103501847 B | 11/2016 |
| CN | 205962844 U | 2/2017 |
| CN | 209807156 U | 12/2019 |
| CN | 105249536 B | 2/2020 |
| CN | 107889450 B | 8/2020 |
| CN | 107949287 B | 4/2021 |
| EP | 0358114 A2 | 3/1990 |
| EP | 0336457 B1 | 12/1994 |
| EP | 2110033 A1 | 10/2009 |
| EP | 1909604 B1 | 12/2009 |
| EP | 1996037 B1 | 4/2012 |
| EP | 2486812 B1 | 6/2014 |
| EP | 2950675 B1 | 10/2017 |
| EP | 2967154 B1 | 10/2018 |
| EP | 2645892 B1 | 3/2019 |
| EP | 3166431 B1 | 3/2019 |
| EP | 2647300 B1 | 4/2019 |
| EP | 2683261 B1 | 5/2019 |
| EP | 2762020 B1 | 5/2019 |
| EP | 3331389 B1 | 5/2019 |
| EP | 3313215 B1 | 6/2019 |
| EP | 3435798 B1 | 4/2020 |
| EP | 3364793 B1 | 8/2020 |
| EP | 3435794 B1 | 9/2020 |
| EP | 3487323 B1 | 9/2020 |
| EP | 3506772 B1 | 9/2020 |
| EP | 3547856 B1 | 9/2020 |
| EP | 3397095 B1 | 11/2020 |
| EP | 3462938 B1 | 11/2020 |
| EP | 3487324 B1 | 11/2020 |
| EP | 3554294 B1 | 11/2020 |
| EP | 3364795 B1 | 12/2020 |
| EP | 3484315 B1 | 12/2020 |
| EP | 3506771 B1 | 12/2020 |
| EP | 3537901 B1 | 12/2020 |
| EP | 3554290 B1 | 12/2020 |
| EP | 3435796 B1 | 1/2021 |
| EP | 3547855 B1 | 1/2021 |
| EP | 3273809 B1 | 2/2021 |
| EP | 3554293 B1 | 2/2021 |
| EP | 3463531 B1 | 3/2021 |
| EP | 3522740 B1 | 3/2021 |
| EP | 3496557 B1 | 4/2021 |
| EP | 3512362 B1 | 4/2021 |
| EP | 3542438 B1 | 4/2021 |
| EP | 3541212 B1 | 5/2021 |
| EP | 3549235 B1 | 5/2021 |
| EP | 3606363 B1 | 5/2021 |
| EP | 3462931 B1 | 6/2021 |
| EP | 3646667 B1 | 7/2021 |
| EP | 3646669 B1 | 7/2021 |
| JP | 2017127649 A | 7/2017 |
| KR | 101611783 B1 | 4/2016 |
| KR | 101824788 B1 | 2/2018 |
| KR | 20180034451 A | 4/2018 |
| KR | 20180083424 A | 7/2018 |
| KR | 20190057399 A | 5/2019 |
| WO | WO-0005976 A1 | 2/2000 |
| WO | WO-2011050964 A1 | 5/2011 |
| WO | WO-2013083635 A1 | 6/2013 |
| WO | WO-2014150979 A2 | 6/2014 |
| WO | WO-2014150979 A2 | 9/2014 |
| WO | WO-2015107551 A2 | 7/2015 |
| WO | WO-2015107552 A1 | 7/2015 |
| WO | WO-2015150068 A1 | 10/2015 |
| WO | WO-2016141556 A1 | 9/2016 |
| WO | WO-2016174179 A1 | 11/2016 |
| WO | WO-2016176800 A1 | 11/2016 |
| WO | WO-2016178098 A2 | 11/2016 |
| WO | WO-2016184247 A1 | 11/2016 |
| WO | WO-2016202304 A1 | 12/2016 |
| WO | WO-2017001352 A2 | 1/2017 |
| WO | WO-2017042081 A1 | 3/2017 |
| WO | WO-2017076590 A1 | 5/2017 |
| WO | WO-2017084818 A1 | 5/2017 |
| WO | WO-2017108394 A1 | 6/2017 |
| WO | WO-2017108429 A1 | 6/2017 |
| WO | WO-2017113513 A1 | 7/2017 |
| WO | WO-2017118135 A1 | 7/2017 |
| WO | WO-2017121296 A1 | 7/2017 |
| WO | WO-2017121546 A1 | 7/2017 |
| WO | WO-2017124957 A1 | 7/2017 |
| WO | WO-2017137510 A1 | 8/2017 |
| WO | WO-2017139963 A1 | 8/2017 |
| WO | WO-2017144861 A1 | 8/2017 |
| WO | WO-2017156695 A1 | 9/2017 |
| WO | WO-2017167513 A1 | 10/2017 |
| WO | WO-2017185051 A1 | 10/2017 |
| WO | WO-2017207416 A1 | 12/2017 |
| WO | WO-2017207419 A1 | 12/2017 |
| WO | WO-2017207443 A1 | 12/2017 |
| WO | WO-2017207586 A1 | 12/2017 |
| WO | WO-2018087738 A1 | 5/2018 |
| WO | WO-2018197515 A1 | 11/2018 |
| WO | WO-2018206615 A2 | 11/2018 |
| WO | WO-2019122015 A1 | 6/2019 |

* cited by examiner

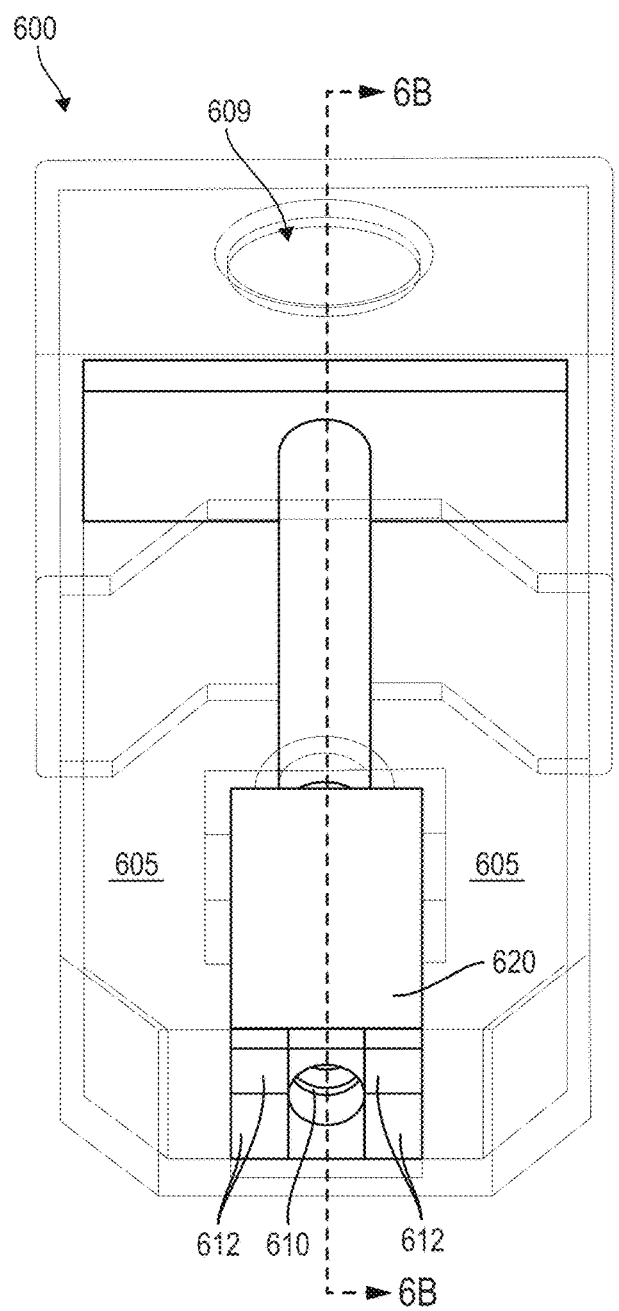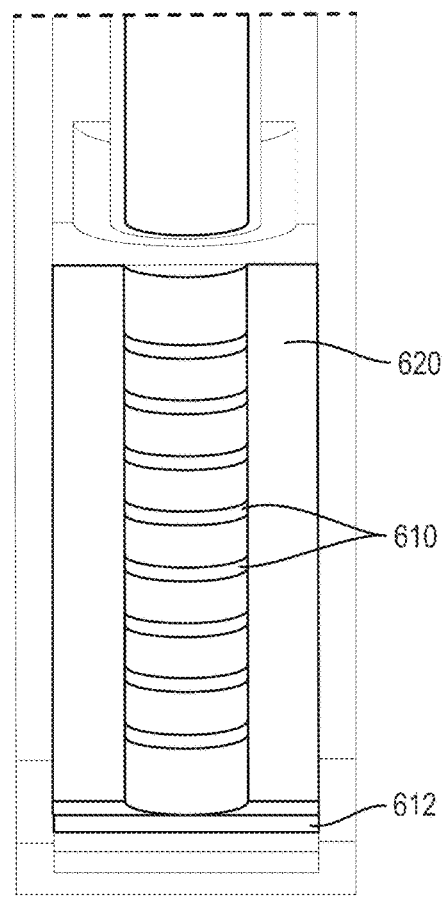
FIG. 6A
FIG. 6B

CARTRIDGES FOR VAPORIZER DEVICES

CROSS-REFERENCE TO RELATED APPLICATIONS

This application claims priority to U.S. Provisional Patent Application Nos. 62/848,681, filed on May 16, 2019, and 62/682,144, filed on Jun. 7, 2018, each entitled "Porous Substrate Surface Heater," the disclosures of which are incorporated herein by reference in their entirety.

BACKGROUND

Vaporizing devices, including electronic vaporizers or e-vaporizer devices, allow the delivery of vapor containing one or more active ingredients by inhalation of the vapor. Electronic vaporizer devices are gaining increasing popularity both for prescriptive medical use, in delivering medicaments, and for consumption of nicotine, tobacco, other liquid-based substances, and other plant-based smokeable materials, such as *cannabis*, including solid (e.g., loose-leaf) materials, solid/liquid (e.g., suspensions, liquid-coated) materials, wax extracts, and prefilled pods (cartridges, wrapped containers, etc.) of such materials. Electronic vaporizer devices in particular may be portable, self-contained, and convenient for use.

SUMMARY

Aspects of the current subject matter relate to cartridges for use in vaporizer or vaporization devices, vaporizer or vaporization devices, atomizer components, and methods.

In one exemplary aspect, a cartridge can include a reservoir housing including a reservoir chamber configured to selectively hold a vaporizable material, and an atomizer in fluid communication with the reservoir chamber. The atomizer includes a porous substrate configured to draw the vaporizable material from the reservoir chamber, and at least one surface heater configured to heat at least a portion of vaporizable material drawn into the porous substrate into a vaporized vaporizable material. The porous substrate includes at least one vent extending therethrough, in which the at least one vent is configured to allow the passage of air into the reservoir chamber in response to the withdrawal of at least a portion of the vaporizable material from the reservoir chamber. The at least one surface heater includes at least one electrically conductive layer deposited on a portion of the porous substrate.

The porous substrate can have a variety of configurations. In some aspects, the porous substrate can extend from a first surface to a second surface that is opposite the first surface. The at least the first surface can be positioned within the reservoir chamber and the at least one electrically conductive layer can be deposited on the second surface.

The at least one vent can have a variety of configurations. In some aspects, the at least one vent can have a first portion with a first cross-sectional area and a second portion with a second cross-sectional area that is less than the first cross-sectional area. In such aspects, the first portion can be adjacent to the reservoir chamber and the second portion can be distal to the reservoir chamber.

In another exemplary aspect, a vaporizer device is disclosed. The vaporizer device can include a vaporizer body that includes a first airflow path; and the cartridge as described above. The cartridge is selectively coupled to the vaporizer body, in which at least a portion of the atomizer is exposed to the first airflow path and the at least one vent is in fluid communication with the first airflow path.

In some aspects, the cartridge can include a second airflow path that is in fluid communication with the first airflow path.

In another exemplary aspect, a cartridge can include a reservoir housing including a reservoir chamber configured to selectively hold a vaporizable material, and an atomizer in fluid communication with the reservoir chamber. The atomizer includes a substrate having a channel extending at least partially therethrough, in which the channel is configured to receive a predetermined volume of vaporizable material from the reservoir chamber at a predetermined rate. The atomizer also includes at least one surface heater that is configured to selectively heat at least a portion of the vaporizable material received within the channel into a vaporized vaporizable material.

The at least one surface heater can have a variety of configurations. In some aspects, the at least one surface heater can include at least one electrically conductive layer deposited on a portion of the substrate. In other aspects, the at least one surface heater can include a first surface heater positioned on a first portion of the substrate, and a second surface heater positioned on a second portion of the substrate.

The substrate can have a variety of configurations. In some aspects, the substrate can have at least two spaced apart surfaces that each define a boundary of the channel. The substrate can include a base that extends between the at least two spaced apart surfaces, in which the base further defines the boundary of the channel. In such aspects, the substrate can be formed as a unitary structure.

In other aspects, the substrate can include first and second sidewalls that are spaced apart from one another in a first direction. The first and second sidewalls can each extend from an inner surface to an outer surface, in which each inner surface defines a boundary of the channel. In such aspects, the substrate can include third and fourth sidewalls that are spaced apart from one another in a second direction that is opposite the first direction. The third and fourth sidewalls can each extend from an inner surface to an outer surface, in which each inner surface defines a boundary of the channel.

In some aspects, the substrate can include at least one vent extending from a first surface of the substrate to a second surface of the substrate, in which the second surface being opposite of the first surface.

The at least one vent can have a variety of configurations. In some aspects, the at least one vent can have a first portion with a first cross-sectional area and a second portion with a second cross-sectional area that is less than the first cross-sectional area. In such aspects, the first portion can be adjacent to the reservoir chamber and the second portion can be distal to the reservoir chamber.

In another exemplary aspect, a vaporizer device is disclosed. The vaporizer device can include a vaporizer body that includes a first airflow path, and the cartridge as described above. The cartridge is selectively coupled to the vaporizer body, in which at least a portion of the atomizer is exposed to the first airflow path.

In some aspects, the cartridge can include a second airflow path that can be in fluid communication with the first airflow path.

In another exemplary aspect, a cartridge can include a mouthpiece, a reservoir configured to hold a vaporizable material, and an atomizer component. The atomizer component includes a porous substrate configured to draw the vaporizable material from the reservoir to a vaporization surface exposed to an air flow path, and a surface heater configured to heat the vaporizable material. The porous substrate has a rigid, non-deformable form. The surface heater includes at least one electrically conductive layer deposited on a portion of the porous substrate, in which the vaporization surface includes the portion of the porous substrate.

The porous substrate can have a variety of configurations. In some aspects, the porous substrate can be at least partially contained within the reservoir. In other aspects, the porous substrate can be fully contained within the reservoir, in which the surface heater can be positioned away from the vaporizable material in the reservoir.

In some aspects, the porous substrate can be in fluid communication with the reservoir on surfaces other than the portion on which the surface heater is deposited. In some aspects, the porous substrate can include a plurality of voids dispersed throughout the porous substrate.

In some aspects, the porous substrate can include a stacked configuration formed of a plurality of separate substrates stacked one on top of another. In such aspects, at least a portion of the surface heater can be disposed between two of the plurality of the separate substrates.

In some aspects, the portion of the porous substrate on which the electrically conductive layer is deposited can include a planar surface, a concave surface, or a cylindrical surface.

The at least one electrically conductive layer can have a variety of configurations. In some aspects, the at least one electrically conductive layer can include a trace pattern or a plate. In other aspects, the at least one electrically conductive layer can include a micro-electrical-mechanical systems (MEMS) layer.

In some aspects, the at least one electrically conductive layer can allow for the vaporizable material from the reservoir to pass therethrough. In some aspects, the at least one electrically conductive layer can include one or more electrical contacts for interfacing with one or more respective pins. In such aspects, the one or more electrical contacts can be deposited on a surface of the porous substrate on which a remaining portion of the at least one electrically conductive layer is not deposited.

The mouthpiece can have a variety of configurations. In some aspects, the mouthpiece can be disposed at a first end of a body of the cartridge and the heating element can be disposed at a second end of the body, opposite the first end.

In some aspects, the cartridge can include an air inlet passage configured to direct a flow of air along the vaporization surface in the air flow path such that when the surface heater is activated, the vaporizable material drawn by the porous substrate along the vaporization surface can be evaporated into the flow of air.

In another exemplary aspect, a vaporization device is disclosed. The vaporization device can include a reservoir configured to hold a vaporizable material, and an atomizer component. The atomizer component includes a porous substrate configured to draw the vaporizable material from the reservoir to a vaporization surface exposed to an air flow path, and a surface heater configured to heat the vaporizable material. The porous substrate has a rigid, non-deformable form. The surface heater includes at least one electrically conductive layer deposited on a portion of the porous substrate, in which the vaporization surface includes the portion of the porous substrate.

The porous substrate can have a variety of configurations. In some aspects, the porous substrate can be at least partially contained within the reservoir. In other aspects, the porous substrate can be fully contained within the reservoir, in which the surface heater can be positioned away from the vaporizable material in the reservoir.

In some aspects, the porous substrate can be in fluid communication with the reservoir on surfaces other than the portion on which the surface heater is deposited. In some aspects, the porous substrate can include a plurality of voids dispersed throughout the porous substrate.

In some aspects, the porous substrate can include a stacked configuration formed of a plurality of separate substrates stacked one on top of another. In such aspects, at least a portion of the surface heater can be disposed between two of the plurality of the separate substrates.

In some aspects, the portion of the porous substrate on which the electrically conductive layer is deposited can include a planar surface, a concave surface, or a cylindrical surface.

The at least one electrically conductive layer can have a variety of configurations. In some aspects, the at least one electrically conductive layer can include a trace pattern or a plate. In other aspects, the at least one electrically conductive layer can include a micro-electrical-mechanical systems (MEMS) layer.

In some aspects, the at least one electrically conductive layer can allow for the vaporizable material from the reservoir to pass therethrough. In some aspects, the at least one electrically conductive layer can include one or more electrical contacts for interfacing with one or more respective pins. In such aspects, the one or more electrical contacts can be deposited on a surface of the porous substrate on which a remaining portion of the at least one electrically conductive layer is not deposited.

In some aspects, the vaporization device can include an air inlet passage configured to direct a flow of air along the vaporization surface in the air flow path such that when the surface heater is activated, the vaporizable material drawn by the porous substrate along the vaporization surface can be evaporated into the flow of air.

In another exemplary aspect, an atomizer component is disclosed. The atomizer component can include a porous substrate configured to draw a vaporizable material from a reservoir, in which the porous substrate has a rigid, non-deformable form, and a surface heater configured to heat the vaporizable material. The surface heater includes at least one electrically conductive layer deposited on a portion of the porous substrate.

The porous substrate can have a variety of configurations. In some aspects, the porous substrate can be at least partially contained within the reservoir. In other aspects, the porous substrate can be fully contained within the reservoir, in which the surface heater can be positioned away from the vaporizable material in the reservoir.

In some aspects, the porous substrate can be in fluid communication with the reservoir on surfaces other than the portion on which the surface heater is deposited. In some aspects, the porous substrate can include a plurality of voids dispersed throughout the porous substrate.

In some aspects, the porous substrate can include a stacked configuration formed of a plurality of separate substrates stacked one on top of another. In such aspects, at least a portion of the surface heater can be disposed between two of the plurality of the separate substrates.

In some aspects, the portion of the porous substrate on which the electrically conductive layer is deposited can include a planar surface, a concave surface, or a cylindrical surface.

The at least one electrically conductive layer can have a variety of configurations. In some aspects, the at least one electrically conductive layer can include a trace pattern or a plate. In other aspects, the at least one electrically conductive layer can include a micro-electrical-mechanical systems (MEMS) layer.

In some aspects, the at least one electrically conductive layer can allow for the vaporizable material from the reservoir to pass therethrough. In some aspects, the at least one electrically conductive layer can include one or more electrical contacts for interfacing with one or more respective pins. In such aspects, the one or more electrical contacts can be deposited on a surface of the porous substrate on which a remaining portion of the at least one electrically conductive layer is not deposited.

In some aspects, the porous substrate can be configured to draw the vaporizable material from the reservoir to a vaporization surface exposed to an air flow path. In such aspects, the atomizer component can include an air inlet passage configured to direct a flow of air along the vaporization surface in the air flow path such that when the surface heater is activated, the vaporizable material drawn by the porous substrate along the vaporization surface can be evaporated into the flow of air.

In another exemplary aspect, a method is disclosed. The method can include drawing, through a porous substrate, a vaporizable material from a reservoir of a vaporization device to a vaporization surface, in which the porous substrate has a rigid, non-deformable form on at least a portion of which a surface heater that includes at least one electrically conductive layer is deposited. The porous substrate is in direct fluid communication with at least a portion of the reservoir, and the surface heater is not in direct fluid communication with the reservoir and is directly along an air flow path. The method also includes heating the vaporization surface with the surface heater to cause vaporization of the vaporizable material, and causing the vaporized vaporizable material to be entrained in a flow of air along the air flow path to a mouthpiece of the vaporization device.

The porous substrate can have a variety of configurations. In some aspects, the porous substrate can be at least partially contained within the reservoir. In other aspects, the porous substrate can be fully contained within the reservoir, in which the surface heater can be positioned away from the vaporizable material in the reservoir.

In some aspects, the porous substrate can be in fluid communication with the reservoir on surfaces other than the portion on which the surface heater is deposited. In some aspects, the porous substrate can include a plurality of voids dispersed throughout the porous substrate.

In some aspects, the porous substrate can include a stacked configuration formed of a plurality of separate substrates stacked one on top of another. In such aspects, at least a portion of the surface heater can be disposed between two of the plurality of the separate substrates.

In some aspects, the portion of the porous substrate on which the electrically conductive layer is deposited can include a planar surface, a concave surface, or a cylindrical surface.

The at least one electrically conductive layer can have a variety of configurations. In some aspects, the at least one electrically conductive layer can include a trace pattern or a plate. In other aspects, the at least one electrically conductive layer can include a micro-electrical-mechanical systems (MEMS) layer.

In some aspects, the at least one electrically conductive layer can allow for the vaporizable material from the reservoir to pass therethrough. In some aspects, the at least one electrically conductive layer can include one or more electrical contacts for interfacing with one or more respective pins. In such aspects, the one or more electrical contacts can be deposited on a surface of the porous substrate on which a remaining portion of the at least one electrically conductive layer is not deposited.

The mouthpiece can have a variety of configurations. In some aspects, the mouthpiece can be disposed at a first end of a body of the cartridge and the heating element can be disposed at a second end of the body, opposite the first end.

The details of one or more variations of the subject matter described herein are set forth in the accompanying drawings and the description below. Other features and advantages of the subject matter described herein will be apparent from the description and drawings, and from the claims.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 6A is a perspective view of another exemplary embodiment of a cartridge with a surface heater and a porous substrate consistent with implementations of the current subject matter;

FIG. 6B is a cross-sectional view of a portion of the cartridge of FIG. 6A taken at line 6B-6B;

DETAILED DESCRIPTION

Figure 1:
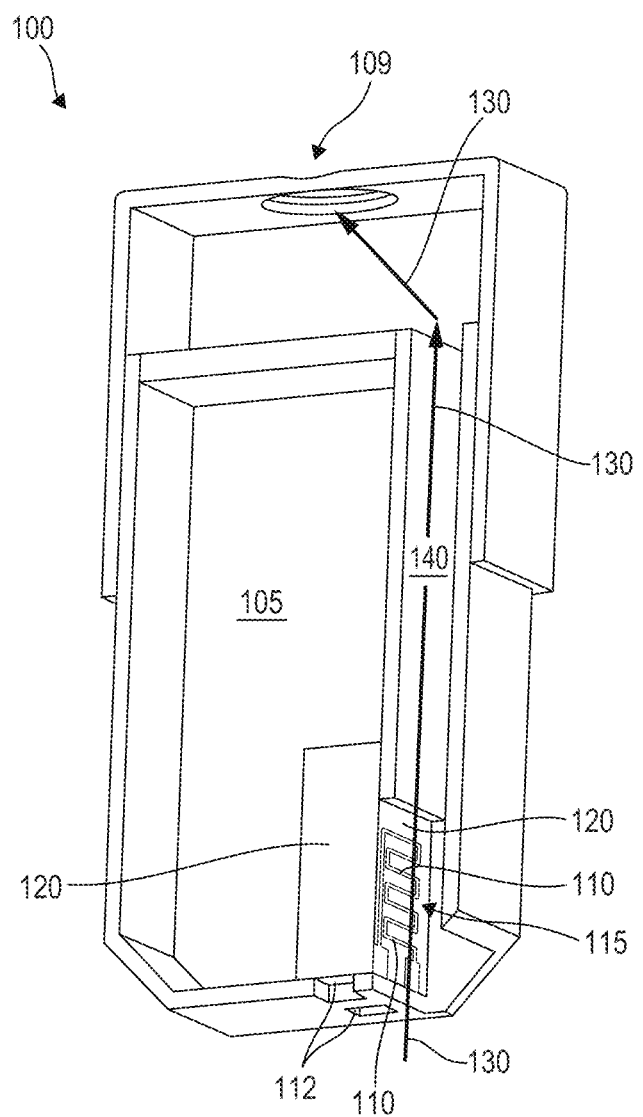
FIG. 1 is a cross-sectional perspective view of one exemplary embodiment of cartridge in which a surface heater and a porous substrate are incorporated consistent with implementations of the current subject matter.

Implementations of the current subject matter include devices relating to vaporizing of one or more materials for inhalation by a user. The term "vaporizer" is used generically in the following description and refers to a vaporization or vaporizer device. Examples of vaporizers consistent with implementations of the current subject matter include electronic vaporizers, electronic cigarettes, e-cigarettes, or the like. In general, such vaporizers are often portable, frequently hand-held devices that heat a vaporizable material to provide an inhalable dose of the material.

Electronic vaporizers typically use a basic atomizer system that includes a wicking element (or wick) with a resistive heating element such as a coil (e.g., a nickel-chromium alloy coil) wrapped around the wicking element or positioned within a hollow wicking element. Other wick configurations are also possible, as discussed further below. The wick can serve at least one or more purposes, including: to draw liquid from a reservoir to the atomizer where it can be vaporized by the coil, to allow air to enter the reservoir to replace the volume of liquid removed, and potentially other purposes. When a user inhales on the vaporizer, the coil heater may be activated, and incoming air passes over the saturated wick/coil assembly, stripping off vapor, which can pass through the user's mouth, entering the user's lungs. During and/or after the puff, capillary action pulls more liquid into the wick and air can return to the reservoir through the wick.

Traditionally, vaporizer devices have utilized a wick typically formed of silica, cotton, or fiberglass material. The traditional silica wick material is formed by bundling together fine, continuous filaments of, for example, silica glass, first into threads, which are then bundled together to form the cord or rope used as the wick. The cord may typically be specified by a nominal outer diameter, number of threads, and/or a value indicating a linear density.

However, this traditional atomizer system, in which liquid is drawn into the wick from a reservoir, is limited in that the liquid is drawn in longitudinally at end points of the cord (e.g., at end points of the continuous filaments of silica). During use of a vaporizer device, liquid may not be replenished as quickly as desired for a user as the liquid evaporates from a heated region of the wick and more liquid needs to travel along the length of the wick for replenishment. Improvements on the liquid delivery rate of such designs may be desirable.

Traditional atomizer systems can present certain other issues. For example, a traditional atomizer system may be fairly complex with many components, and there may be significant variability in the manufacturing and use of the wick and the coil components. Moreover, the wick, formed as described above by bundling together fine, continuous filaments first into threads, which are then bundled together to form the cord or rope used as the wick, may be fragile and its non-rigid structure may require precise and careful placement, increasing the complexity of manufacturing.

In other atomizer designs, the traditional wick and coil design is modified to incorporate a cylindrical ceramic wick, which addresses some design challenges of having a non-rigid wick as well as shortcomings due to the longitudinal draw of liquid. However, such designs can have a number of parts, also potentially leading to manufacturing complexity.

In yet another atomizer design, a chimney coil design is implemented. Such a design utilizes a ceramic wick formed into a hollow tube with a heating coil on an inside portion of the hollow tube. Rather than pulling liquid from a reservoir along an axis of the wick, liquid surrounds the perimeter of the chimney coil, resulting in a large wicking area and a short wicking distance. However, this design can still require a number of parts, which can also lead to manufacturing complexity.

Each of the atomizers described above may include additional challenges in that the designs are not volumetrically compact, and instead tend to occupy a significant portion of the vaporizer device in which they are incorporated.

An atomizer component for a vaporizer device, consistent with features of one or more implementations of the current subject matter, may provide advantages and improvements relative to existing approaches, while also introducing additional benefits as described herein. As used herein, "atomizer component" is used synonymously with "atomizer."

A vaporizer consistent with implementations of the current subject matter may include a vaporizer body or device and a cartridge (also referred to as a pod). The body/device may include a battery, a microcontroller, and an interface to electrically and mechanically connect with the cartridge. The cartridge may generally include a reservoir or reservoir chamber, an air path, and an atomizer component in accordance with implementations of the current subject matter. As used herein, "reservoir" is used synonymously with "reservoir chamber."

An atomizer component consistent with implementations of the current subject matter may be formed of a porous substrate with a surface heater on a surface (referred to herein as a "heated surface") of the substrate. The atomizer can also be integrated into the vaporizer body, that is, without any cartridge, or alternatively, as a heated plate that is part of a vaporizer body positioned to contain a surface of a porous substrate that is part of a cartridge when the cartridge is coupled to the vaporizer body.

In an atomizer design consistent with implementations of the current subject matter, a flattened wick design may be formed of silica, cotton, fiberglass, or other material. Such a design may have favorable wicking properties based on varying geometry, which may also facilitate manufacturing (e.g., based on ease of insertion, ability for di-cutting, etc.). In some implementations, traces may be printed onto the wick. In other implementations, a coil or wire is wrapped around the wick.

FIG. 1 illustrates, via a cross-sectional view, a cartridge 100 in which a surface heater 110 and a porous substrate 120 may be incorporated consistent with some implementations of the current subject matter.

The cartridge 100 may be used with a vaporizer body/device (not shown) having a battery and control circuitry, together configured to generate an inhalable vapor by heating a vaporizable material before and/or as it enters the porous substrate 120 from which it can be vaporized.

In the example configuration shown in FIG. 1, the cartridge 100 includes a reservoir (or tank) 105 for holding a vaporizable material (such as a nicotine e-liquid, or an oil, or some other fluid or liquid having desired vaporizable material), a proximal mouthpiece 109, and an atomizer component situated within or in contact with fluid contained within the reservoir 105. The atomizer component is a monolithic, modular component formed of the porous substrate 120 with the surface heater 110, together creating a heated surface portion 115 of the atomizer component when the surface heater 110 is activated. The atomizer component is, according to some aspects, secured within the cartridge 100 by, for example and not limitation, insert molding, welding (e.g., ultrasonic welding, plastic to ceramic welding, radio-frequency (RF) welding, etc.), a snap-fit connection, a press-fit connection, or by any other secure connection method.

According to some aspects of the current subject matter, the porous substrate 120 is in fluid communication with the reservoir 105 on a number, a majority, or even all surfaces that are not heated (e.g., surfaces other than the heated surface 115). That is, the porous substrate 120 can provide a capillary conduit from the reservoir 105 to the electrical layer (the surface heater 110) not in direct contact with the reservoir 105.

An air path 130 is shown in FIG. 1. Air may be drawn in from the bottom or base of the cartridge 100 and pulled alongside the atomizer component, and in particular the surface heater 110. The air path 130 through the cartridge 100 then passes alongside the reservoir 105 in a passageway 140 situated between an outer sidewall of the reservoir 105 and an inner sidewall of the cartridge 100, leading to a mouthpiece 109. Thus, the atomizer component is directly in the vapor path or air path 130. Other air paths can also be provided, to provide air along the surface heater 110.

The porous substrate 120 draws vaporizable material from the reservoir 105, due to the porosity of the substrate 120 and resultant capillary action. When a user puffs on the mouthpiece 109 of the cartridge 100, air flows into an inlet and along the air path 130. In association with the user puff, the surface heater 110 may be activated, e.g., by automatic detection of the puff via a pressure sensor, by detection of a pushing of a button by the user, by signals generated from a motion sensor, a flow sensor, a capacitive lip sensor, or other approach capable of detecting that a user is taking or about to be taking a puff or otherwise inhaling to cause air to enter the vaporizer device and travel along the air path 130. When the surface heater 110 is activated, a temperature increase results due to current flowing through the surface heater 110 to generate heat. The heat is transferred to some amount of the vaporizable material through conductive, convective, and/or radiative heat transfer such that at least a portion of the vaporizable material vaporizes. The heat transfer can occur to vaporizable material in the reservoir as well as to vaporizable material drawn into the porous substrate. This can, for example, be desired to pre-heat some of the vaporizable material in the reservoir before it is drawn through the porous substrate to the surface heater 110. The air passing into the vaporizer device flows along the air path 130 past the atomizer component, drawing away the vaporized vaporizable material from the porous substrate 120. The vaporized vaporizable material typically then condenses due to cooling, pressure changes, etc., such that it exits the mouthpiece 109 as an aerosol for inhalation by a user.

The porous substrate 120 may be made of a porous ceramic material, a sintered material, other porous materials, such as high-temperature resistant materials including, for example and not limitation, metals, glass, silicon, carbon or high-temperature resistant plastic materials such as, for example and not limitation, polyphenylene sulfide (PPS), liquid crystal polymer (LCP), or polyether ether ketone (PEEK). The porous substrate 120 may be characterized by having a plurality of voids or spaces, allowing for the absorption and transport of liquid from the reservoir 105. The void size, particle size, or porosity of the porous substrate 120 may be chosen based on various factors, for example to achieve desired characteristics or due to specific parameters of the cartridge/device (such as, for example, the viscosity of the vaporizable material and/or other design considerations). The plurality of voids or spaces may be an inherent property of the material (or materials) or may be formed from, for example, drilled (e.g., laser drilled) holes. The porous substrate 120 may be further characterized by having a rigid, non-deformable structure.

According to additional implementations of the current subject matter, combinations of two or more materials may be included in the bulk of the porous substrate, and such combinations can include both homogeneous distributions of the two or more materials throughout the bulk of the porous material or other configurations in which relative amounts of the two or more materials are spatially heterogeneous. For example, in one exemplary configuration, the porous substrate may have a stacked configuration, in which different substrates are stacked one on top of another (either vertically or horizontally). The porosity of this stacked configuration may decrease from top to bottom from within the cartridge (for example, with a most porous material on the top within the reservoir and one or more materials with a lesser porosity outside of the reservoir). This type of stacked configuration may provide for efficient absorption of the vaporizable material in the porous substrate within the reservoir. In various configurations, the porosity of the substrate may be designed such that each layer is specifically manufactured with a specific porosity.

A selection of one or more materials and a configuration (e.g., multiple layers) of the porous substrate 120 may be based on various factors, for example to achieve desired characteristics or due to specific parameters of the cartridge/device (such as, for example, the type of vaporizable material, the vaporization temperature, the desired shot weight for a puff, the dimensions of the porous substrate, and/or the surface area of the surface heater). For example, in implementations of the cartridge designed for use with liquid vaporizable material having a relatively higher viscosity, the pores of the porous substrate can be relatively larger.

The porous substrate 120 may be in a rectangular block shape or a cubic shape. In some implementations, the porous substrate 120 is a thin, rectangular block with the surface heater 110 contained on a rectangular side with the largest surface area. Other shapes are also within the scope of the current subject matter, as further described below. A large surface area for the surface heater 110 may be advantageous for distribution of heat and faster heating.

The surface heater 110 may include one or more electrically conductive layers on or in contact with the porous substrate 120. In some examples, the one or more electrically conductive layers may include a trace pattern deposited on a surface or at least a portion of a surface of the porous substrate 120. A trace pattern may be configured to achieve a desired and controlled electrical resistance, and may or may not be uniform in thickness or extent along the surface of the porous substrate 120. Specific shapes, patterns, thickness, etc. of the surface heater 110 may be advantageous in allowing control of heat delivery to the porous substrate 120 to be controlled and allowing for the liquid from the reservoir 105 to pass through. Alternatively, the electrically conductive layer may be a plate or other continuous layer that covers the entire surface or a portion of the surface of the heated surface 115 of the substrate 120. Such a plate or other continuous layer may include features such as holes, micro-perforations, etc. for allowing vaporizable material from the reservoir 105 to pass through the surface heater 120. The electrically conductive layer may be made from any electrically conductive material, such as, for example and not limitation, a nickel chromium alloy, stainless steel, nickel, platinum, gold, copper, or aluminum. The electrically conductive layer may be a micro-electrical-mechanical systems (MEMS) layer. In this manner, or in other approaches consistent with the current subject matter, a surface heater can be in contact with at least a portion of a surface of the porous substrate, and can be at least part of (e.g., included in) a vaporization surface of the porous substrate.

The surface heater 110 may be adhered to the porous substrate 120 in a number of ways, such as by pulsed laser deposition, physical vapor deposition, chemical vapor deposition, electroplating, electro-less plating, screen printing, or the like. In some variations of the current subject matter, the surface heater 110 may be a stamped part that is snapped onto or otherwise mechanically retained by the porous substrate 120. In other variations, the surface heater 110 may be a stamped part that is insert molded into the porous substrate 120. In other variations, the surface heater 110 is fixed to the porous substrate 120 by any secure attachment method.

In some variations of the current subject matter, the atomizer component may have a single heated surface (e.g., heated surface 115), while in other variations there may be more than one heated surface.

The surface heater 110, in accordance with implementations of the current subject matter, may have areas of lower electrical resistance that can be used as contacts (electrical contacts 112 shown in FIG. 1) for electrically interfacing the cartridge 100 with the vaporizer body/device. The electrical contact areas may be positioned on a surface different than the heated surface 115, while in some variations the electrical contact areas may be on the same surface as the heated surface 115. This configuration of the surface heater 110 with electrical contacts 112 has manufacturing advantages as no additional components are required for the contacts and no bridge may be necessary within the cartridge. Moreover, the rigidity of the porous substrate on which the electrical contacts are formed provides a solid contact surface for connection with contact pins (e.g., pogo pins or leaf spring pins of a vaporizer body/device which need to connect with the electrical contacts of a cartridge for operation, as further described below).

In accordance with some implementations of the current subject matter, the heated surface 115 (and other heated surfaces if any) are in the air path 130.

In accordance with some implementations of the current subject matter, the surface heater 110 may have one or more holes or openings that align with one or more corresponding pores of the porous substrate 120.

Figure 2A:
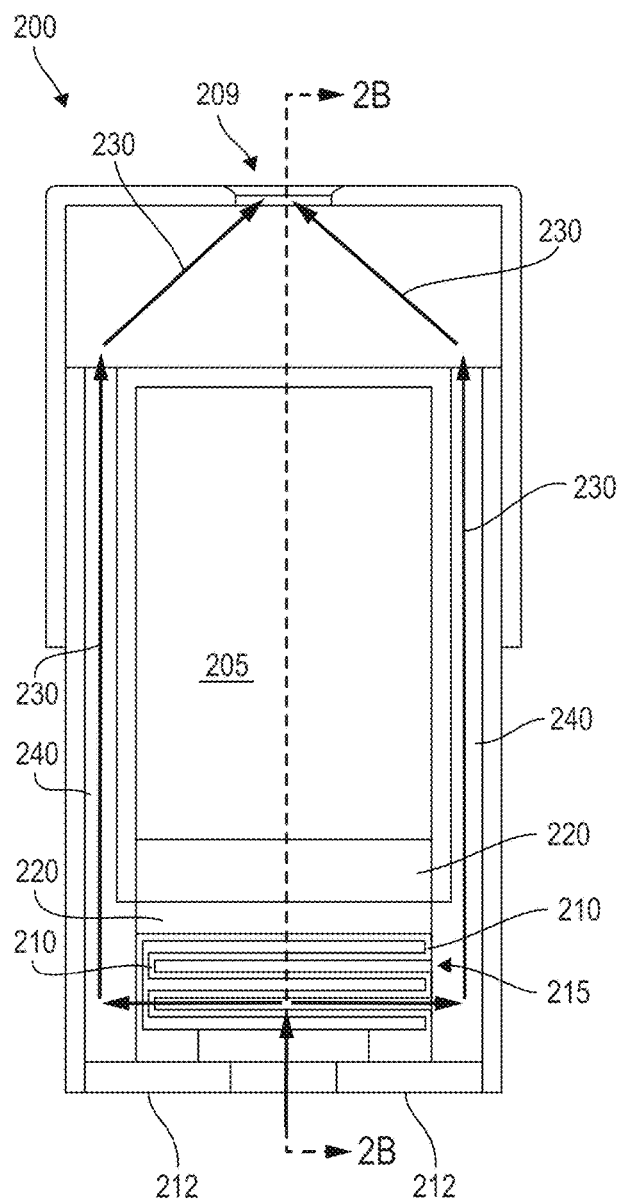
FIG. 2A is cross-sectional front view of another exemplary embodiment of a cartridge in which a surface heater and a porous substrate are incorporated consistent with implementations of the current subject matter.
Figure 2B:
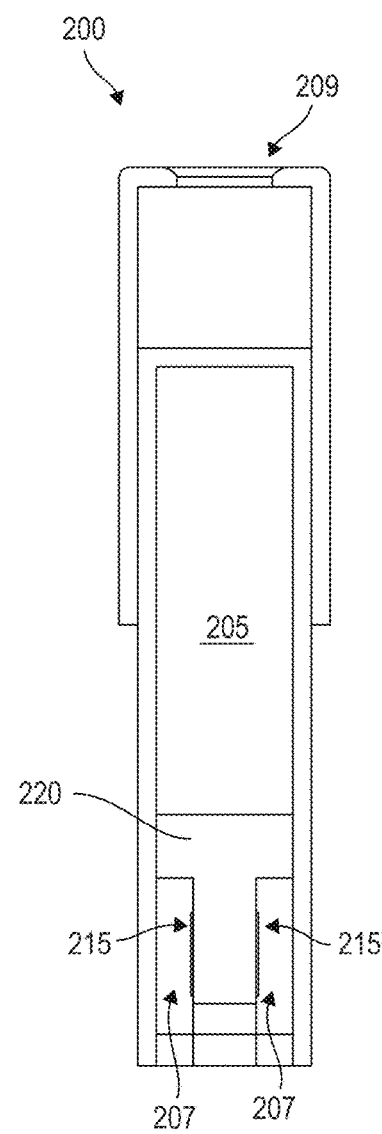
FIG. 2B is a cross-sectional side view of the cartridge of FIG. 2A taken at 2B-2B.

FIGS. 2A and 2B illustrate, via cross-sectional front and side views, respectively, a cartridge 200 in which a surface heater 210 and a porous substrate 220 are incorporated consistent with additional implementations of the current subject matter.

In the example configuration shown in FIG. 2A, the cartridge 200 includes a reservoir (or tank) 205, a proximal mouthpiece 209, and an atomizer component situated partially within the reservoir 205 and formed of the porous substrate 220 with the surface heater 210. As shown in FIG. 2B, the surface heater 210 may be situated on two opposing sides of the porous substrate 220, thereby creating two heated surface portions 215 when the surface heater 210 is activated.

As shown in FIGS. 2A and 2B, a portion of the porous substrate 220 extends into the reservoir 205, and the surface heater 210 is affixed to one or more side portions of the porous substrate 220 that are not in direct fluid communication with the reservoir 205. Voids 207 (shown in FIG. 2B) are formed in the reservoir on either side of the substrate 220/heater 210 in areas in which there is no vaporizable material. Also shown in FIG. 2A are electrical contacts 212. The electrical contacts 212 are positioned such that contact is easily made with contact pins (e.g., pogo pins or leaf spring pins of a vaporizer body/device which need to connect with the electrical contacts 212 of the cartridge 200 for operation).

An air path 230 is shown in FIG. 2A. Air may be drawn in from the bottom or base of the cartridge 200 and pulled over the surface heater 210 (passing through the voids 207). The air path 230 through the cartridge 200 then passes alongside the reservoir 205 in one or more passageways 240 situated between an outer sidewall of the reservoir 205 and an inner sidewall of the cartridge 200, leading to the mouthpiece 209.

Figure 3A:
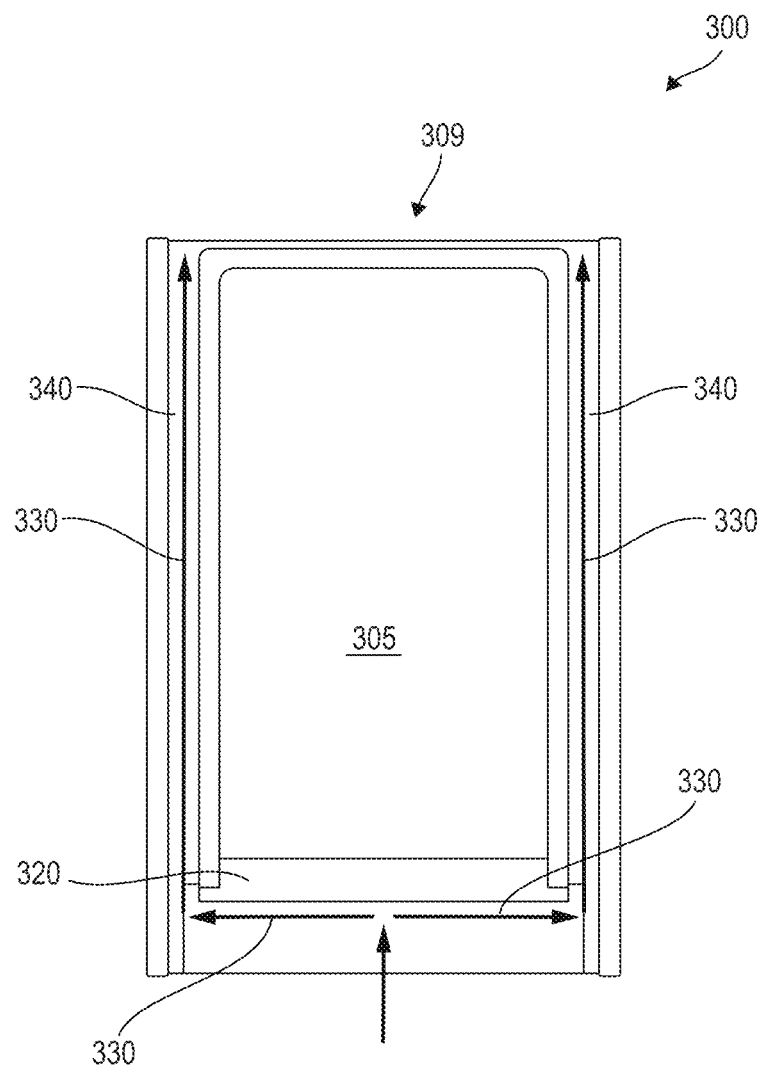
FIG. 3A is a cross-sectional front view of another exemplary embodiment of a cartridge in which a surface heater and a porous substrate are incorporated consistent with implementations of the current subject matter.
Figure 3B:
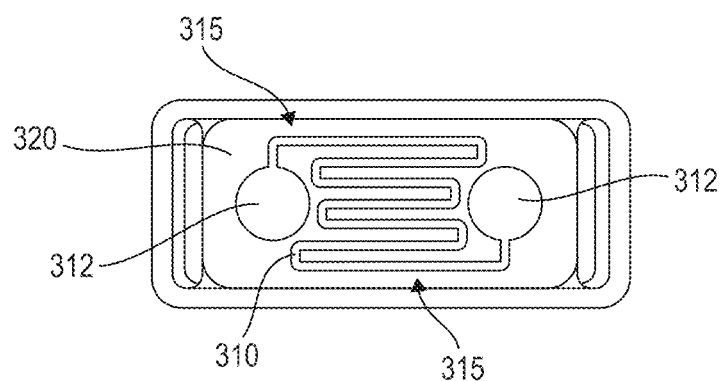
FIG. 3B is a bottom view of the cartridge of FIG. 3A.
Figure 4A:
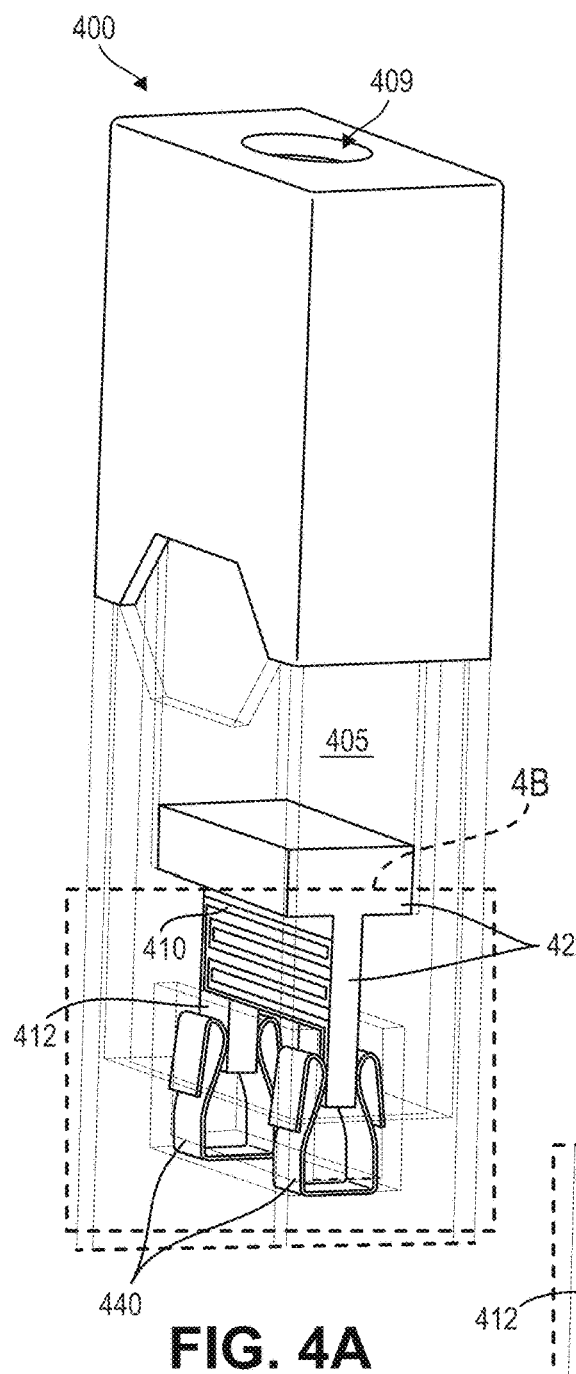
FIG. 4A is a partially transparent perspective view of another exemplary embodiment of a cartridge with a surface heater and a porous substrate and connection with contact pins consistent with implementations of the current subject matter.
Figure 4B:
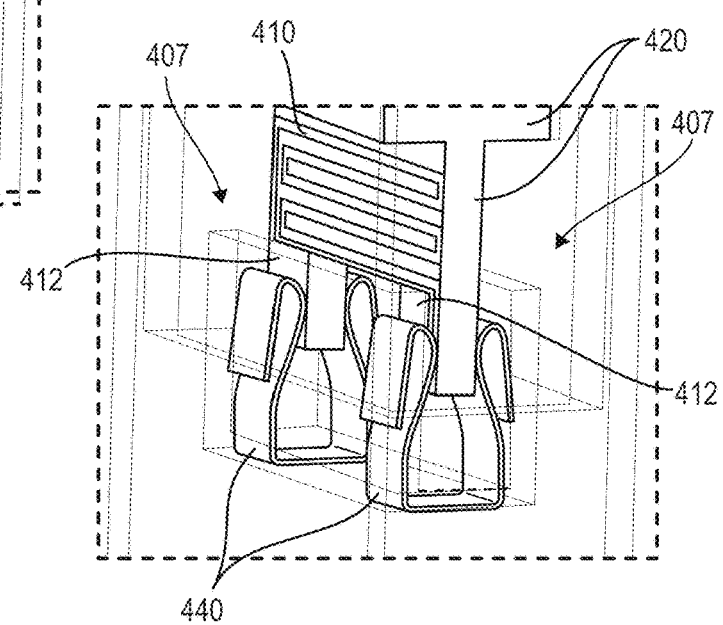
FIG. 4B is a magnified view of the cartridge of FIG. 4A taken at 4B.

FIGS. 3A and 3B illustrate, via a cross-sectional front view and a bottom view, in which a surface heater 310 and a porous substrate 320 are incorporated consistent with further implementations of the current subject matter.

In the example configuration shown in FIG. 3A, the cartridge 300 includes a reservoir (or tank) 305, a proximal mouthpiece 309, and an atomizer component situated at a bottom portion of the reservoir 305 and formed of the porous substrate 320 with the surface heater 310. As shown in FIB. 3B, the surface heater 310 is situated on a bottom portion of the porous substrate 320 opposite the reservoir 305, thereby creating a heated surface portion 315 on the bottom portion of the porous substrate 320 when the surface heater 310 is activated. Also shown in FIG. 3B are electrical contacts 312. The electrical contacts 312 are sized and shaped for connection with contact pins (e.g., pogo pins or leaf spring pins of a vaporizer body/device which need to connect with the electrical contacts 312 of the cartridge 300 for operation).

An air path 330 is shown in FIG. 3A. Air may be drawn in from the bottom or base of the cartridge 300, contacting the surface heater 310 and the bottom portion of the porous substrate 320. The air path 330 through the cartridge 300 then passes alongside the reservoir 305 in one or more passageways 340 situated between an outer sidewall of the reservoir 305 and an inner sidewall of the cartridge 300, leading to the mouthpiece 309. It should be apparent to one of skill in the art, that the porous substrate 320 can be configured to completely fill the bottom portion of the reservoir 305, or can be a smaller-sized porous substrate contained within a larger frame of some material that is not porous. This can be done, for example, to appropriately tune the amount of vaporized material that a user draws in each puff.

FIGS. 4A-4B and 5A-5B illustrate, via various perspective views, features of cartridges 400, 500 including connection with contact pins 440, 540. Features of cartridges 400 and 500 (and the porous substrates/surface heaters) are similar to that of cartridge 200 (and the porous substrate 220/surface heater 210) described above. Air flow through the cartridges 400 and 500 is similar to that described with respect to the cartridge 200.

Cartridge 400 includes a reservoir (or tank) 405, a proximal mouthpiece 409, and an atomizer component situated partially within a bottom portion of the reservoir 405. The atomizer component is formed of a porous substrate 420 (having a similar structure to, and operation of, the porous substrate 220 of FIGS. 2A and 2B) with a surface heater 410. As shown, an upper portion of the porous substrate 420 is contained within the reservoir 405, while a bottom portion, on which the surface heater 410 and electrical contacts 412 (on extending tabs of the porous substrate 420) are contained, is outside of the reservoir 405. Voids 407 (shown in FIG. 4B) are formed in the reservoir 405 on either side of the substrate 420/heater 410 in areas in which there is no vaporizable material. The electrical contacts 412 provide for electrically interfacing the cartridge 400 with a vaporizer body/device through contact with contact pins 440 that are of a leaf spring configuration. The rigidity of the porous substrate 420 on which the electrical contacts 412 are positioned provides for a solid contact surface for connection with the contact pins 440.

Figure 5A:
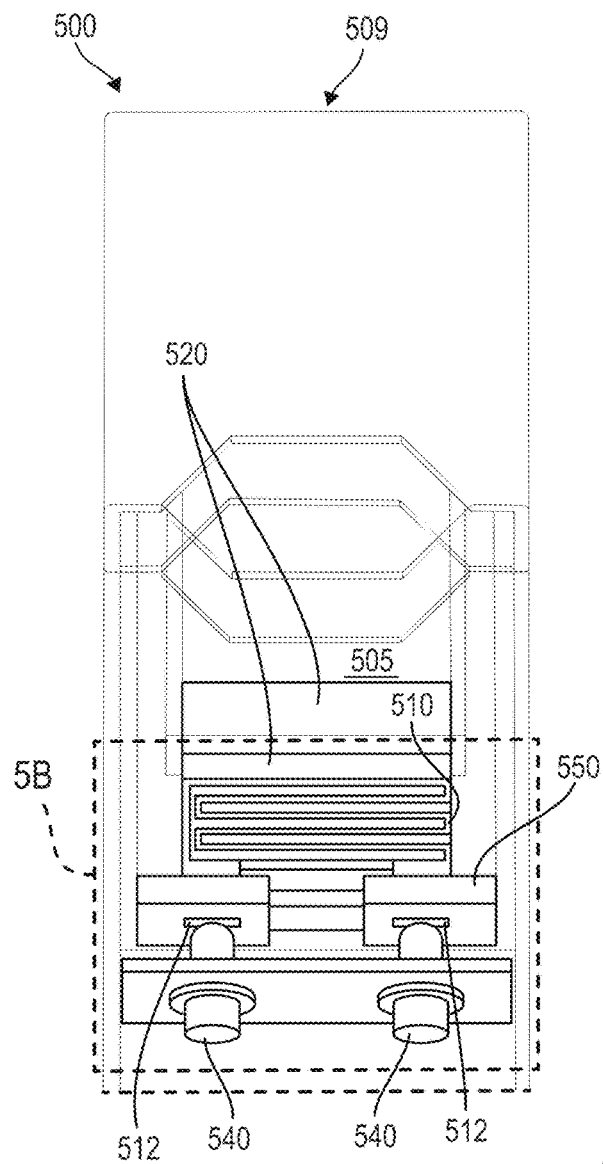
FIG. 5A is a partially transparent perspective view of another exemplary embodiment of a cartridge with a surface heater and a porous substrate and connection with contact pins consistent with implementations of the current subject matter.
Figure 5B:
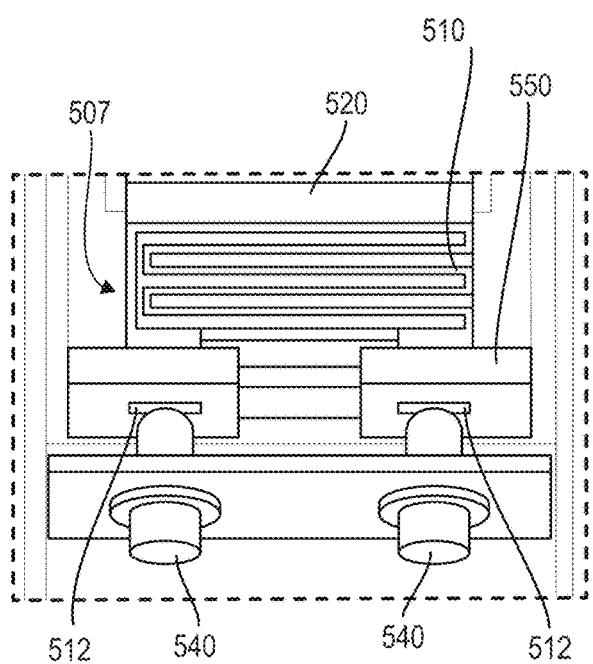
FIG. 5B is a magnified view of the cartridge of FIG. 5A taken at 5B.

Cartridge 500 has a similar structure to that of cartridge 400: a reservoir (or tank) 505, a proximal mouthpiece 509, and an atomizer component situated partially within a bottom portion of the reservoir 505. The atomizer component is formed of a porous substrate 520 with a surface heater 510. As shown, an upper portion of the porous substrate 520 is contained within the reservoir 505, while a bottom portion, on which the surface heater 510 is contained, is outside of the reservoir 505. Voids 507 (one of which is shown in FIG. 5B) are formed in the reservoir 505 on either side of the substrate 520/heater 510 in areas in which there is no vaporizable material. In this configuration, electrical contacts 512 extend from the surface heater 510 and through a support structure 550, with bottom edges of the electrical contacts 512 exposed and/or accessible at a bottom portion of the support structure 550. The electrical contacts 512 make contact with contact pins 540, which in this configuration may be in a pogo pin form.

As mentioned above, in some implementations of the current subject matter, a porous substrate may have a geometry other than that of a planar surface. For example, the porous substrate may have one or more concave or convex regions (e.g., curved or triangular) on which the surface heater is positioned (e.g., deposited). One or more concave regions can allow for a greater surface area for the heated surface within a smaller footprint. The other surfaces (e.g., the sides other than the heated surface or surfaces) of the porous substrate may be flat, concave, convex, a combination thereof, or other geometries. One example of such a configuration is shown in FIGS. 6A and 6B, in which a cartridge 600, with a mouthpiece 609, includes a porous substrate 620 within a reservoir 605. The porous substrate 620 has two concave regions on which a surface heater 610 is positioned. In some embodiments, the surface heater 610 may be formed on just one of the concave regions. The surface heater 610 can be deposited directly to each concave side. The two concave regions can be joined together to form an open cylinder. In some implementations, the two concave regions can be fully separable and not electrically connected. A bottom region of the porous substrate 620 (e.g., a bottom end of the open cylinder) is outside of the reservoir 605 or otherwise positioned away from any liquid held within the reservoir 605. Electrical contacts 612 may be formed on a bottom region of the porous substrate 620. While the surface heater 610 is shown with electrical traces arranged in a horizontal configuration (e.g., electrical traces are orthogonal to the direction of airflow), other configurations, such as vertically-oriented (e.g., parallel to the direction of airflow), a helical configuration, a zig-zag configuration, or other patterns or arrangements, are possible. The traces can be connected in series or in parallel.

In other configurations, in accordance with an implementation of the current subject matter, rather than one or more concave regions forming an open cylinder, a porous substrate may be in the form of a half-pipe configuration or the like, which may be formed from a single substrate or from two or more profiles joined together to form the half-pipe. Such a configuration may be similar to the porous substrate shown in FIG. 6B. The porous substrate is situated so that the concave region on which the electrical traces are deposited is away from any vaporizable material held in the reservoir. For example, the porous substrate may be positioned in a corner of the reservoir in contact with a wall of the reservoir, away from the liquid held within (such as the position of the porous substrate shown in FIG. 1, for example). In such a configuration, a cap, plug, plate, or the like may form a top seal.

In another embodiment, the half-pipe chimney may be substantially centralized within the reservoir (similar to the position of the porous substrate shown in FIG. 6A), but where an opposing side of the concave region is not part of the porous substrate but is adhered or otherwise joined to the porous substrate to form a half-pipe cylinder for the airflow path.

Figure 7A:
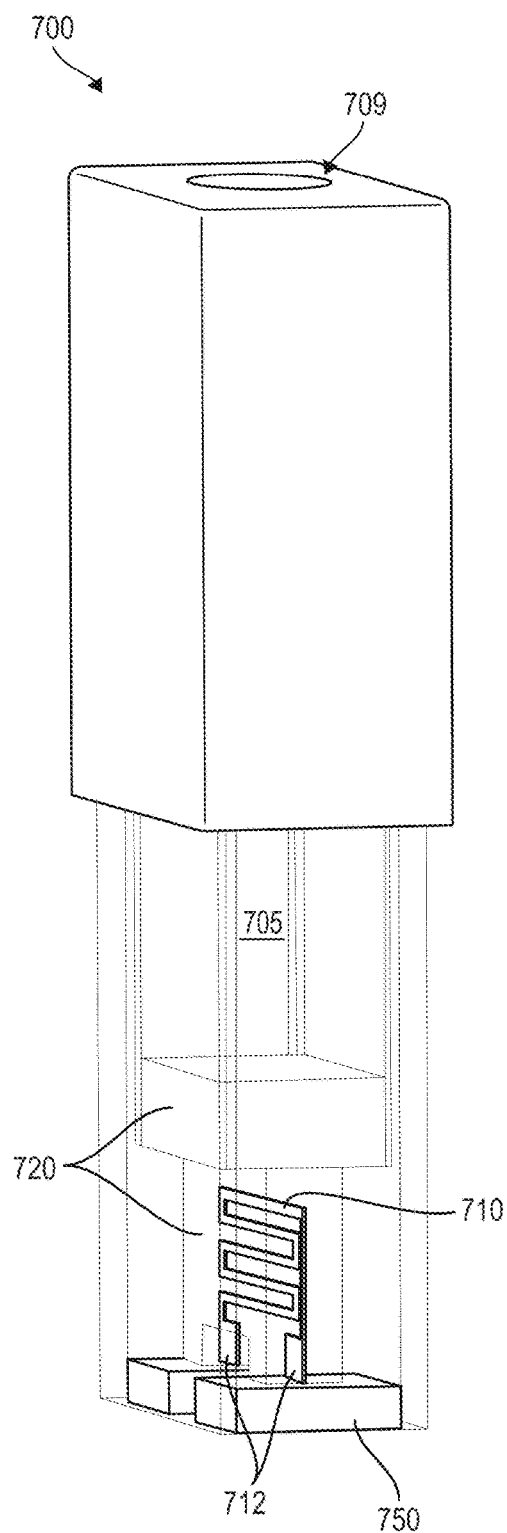
FIG. 7A is a perspective view of another exemplary embodiment of a cartridge with a surface heater and a porous substrate consistent with implementations of the current subject matter.
Figure 7B:
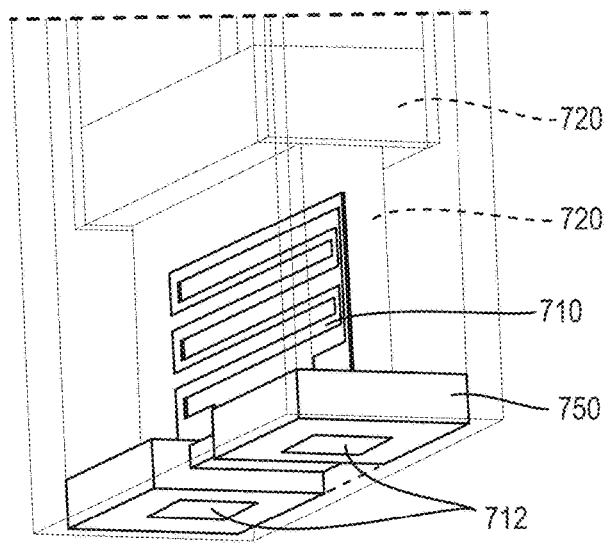
FIG. 7B is a perspective of a portion of the cartridge of FIG. 7A.

As described above, in some exemplary configurations, the porous substrate may be stacked (either vertically or horizontally) with two or more layers such that the heater is contained within the porous substrate between two of the layers. In other configurations, the surface heater may be embedded within a portion of the porous substrate. An example of such a configuration is shown in FIGS. 7A and 7B, in which a cartridge 700 with mouthpiece 709 is illustrated. In this configuration, a top portion of a porous substrate 720 is contained within a reservoir 705, while a bottom portion in which a surface heater 710 is embedded (or placed between stacks) is contained outside of the reservoir 705. Electrical contacts 712 extend from the surface heater 510 and through a support structure 750, providing for contact with contact pins.

Figure 8A:
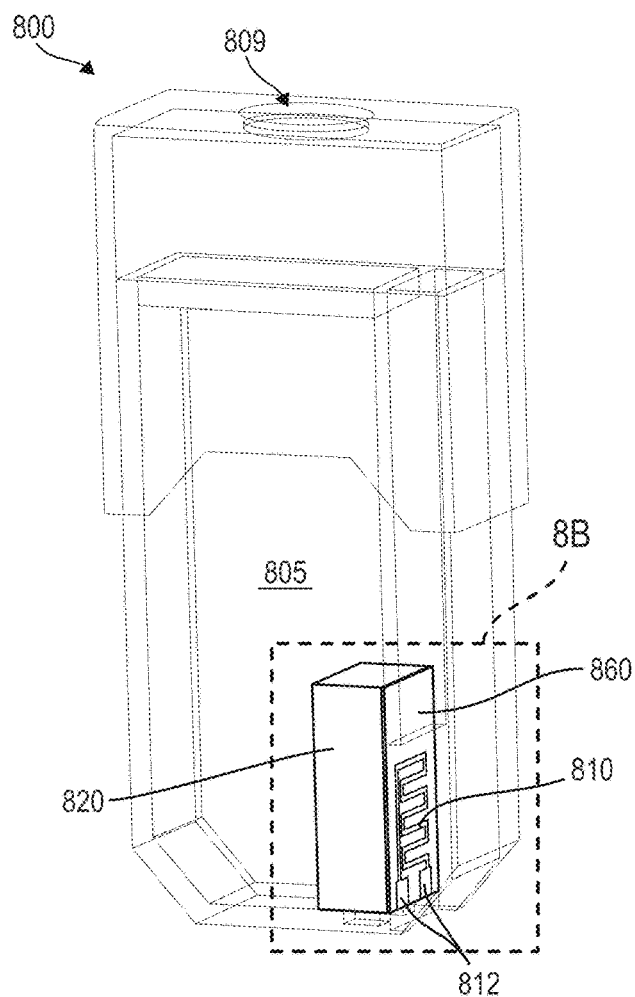
FIG. 8A is a perspective view of another exemplary embodiment of a cartridge with a surface heater and a porous substrate consistent with implementations of the current subject matter.
Figure 8B:
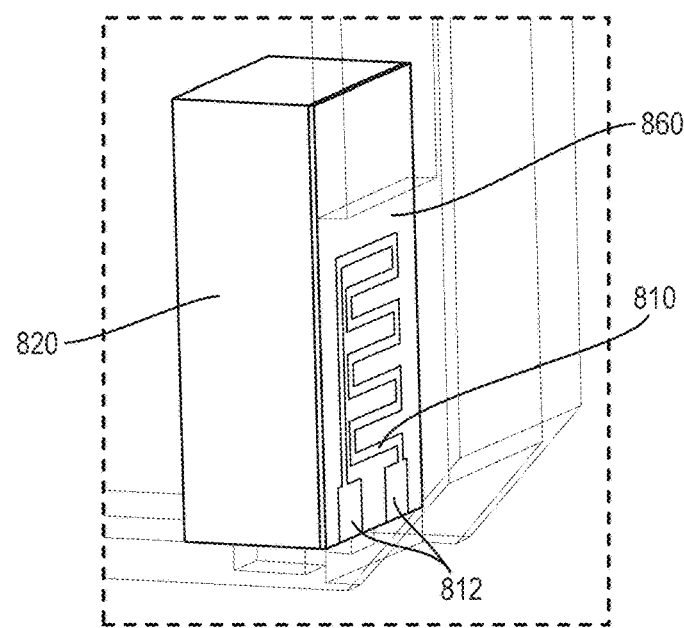
FIG. 8B is a magnified view of the cartridge of FIG. 8A taken at 8B.

FIGS. 8A and 8B illustrate, via perspective views, features of cartridge 800 with mouthpiece 809 including an insulating layer 860 in contact with or adhered to portions of a porous substrate 820. In this configuration, a surface heater 810 is deposited on an outer surface of the insulating layer 860, on a side away from fluid communication with contents of reservoir 805. Electrical contacts 812 are also provided. The insulating layer 860 serves to electrically isolate the surface heater 810 from the porous substrate 820 while also, due to some level of porosity, allowing for vaporizable material from the reservoir 805 drawn into the porous substrate 820 to pass through to be heated and condensed. The surface heater 810 may be adhered to the insulating layer 860 in the same manner as described above with respect to a surface heater being adhered to a porous substrate. In some implementations, the insulating layer is deposited on the porous substrate, and the electrical layer (the surface heater) is deposited on the insulating layer, with one or more portions of the insulating layer ablated to provide or increase porosity.

Figure 9A:
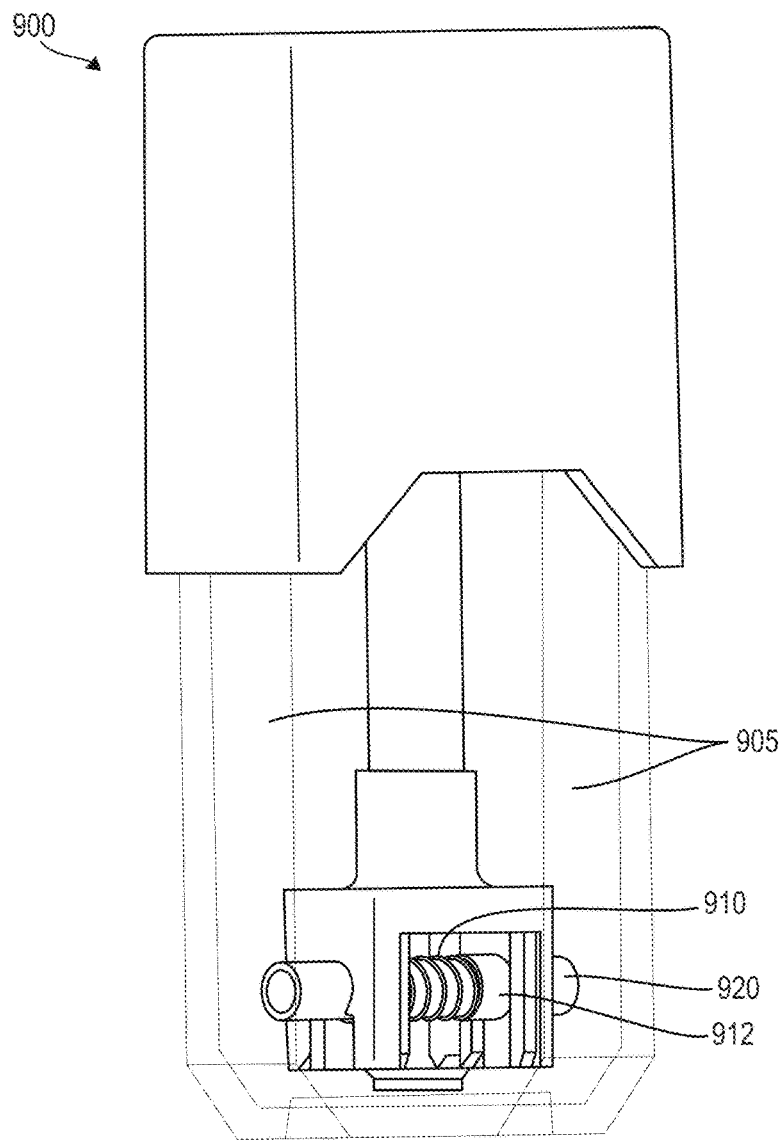
FIG. 9A is a perspective view of another exemplary embodiment of a cartridge with a surface heater and a porous substrate consistent with implementations of the current subject matter.
Figure 9B:
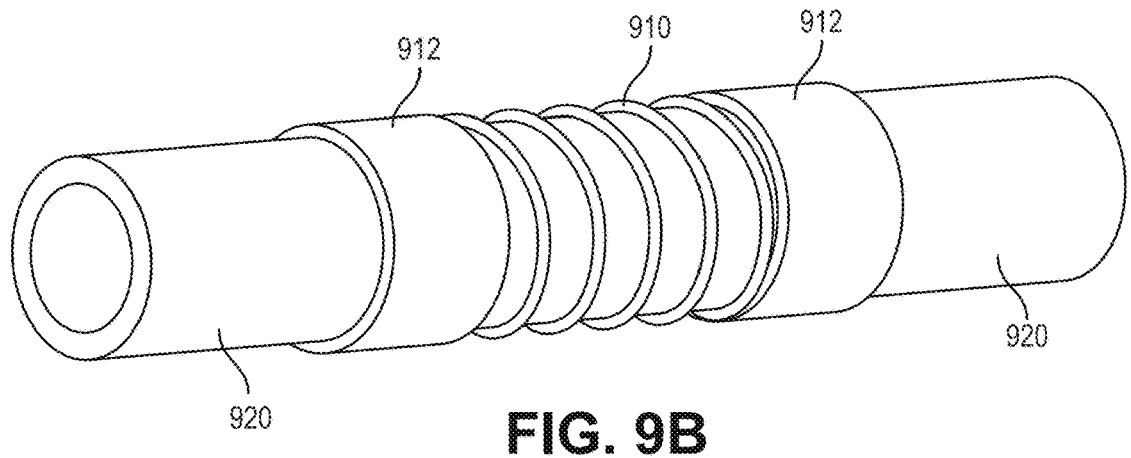
FIG. 9B is a perspective view of the surface heater and porous substrate of FIG. 9A.

According to an implementation of the current subject matter, a porous substrate may be in the shape of a cylinder with the surface heater screen-printed or otherwise deposited on an outside portion of the cylinder. One example of such a configuration is illustrated in FIGS. 9A and 9B in which cartridge 900 with reservoir 905 includes a tubular porous substrate 920 with a surface heater 910 and electrical contacts 912 adhered (e.g., deposited) on an outer portion of the porous substrate 920. As shown, two end regions of the porous substrate 920 extend into the reservoir 905 to be in direct fluid communication with a vaporizable material contained therein. The portion on which the surface heater 910 and electrical contacts 912 are adhered is not in direct fluid communication with the reservoir 905. The porous substrate 920 draws vaporizable material from the reservoir 905, due to the porosity of the substrate 920 and resultant capillary action. That is, the porous substrate 920 is a capillary conduit in the reservoir 905 with the electrical layer (the surface heater 910) not in capillary communication with the reservoir 905.

Figure 10:
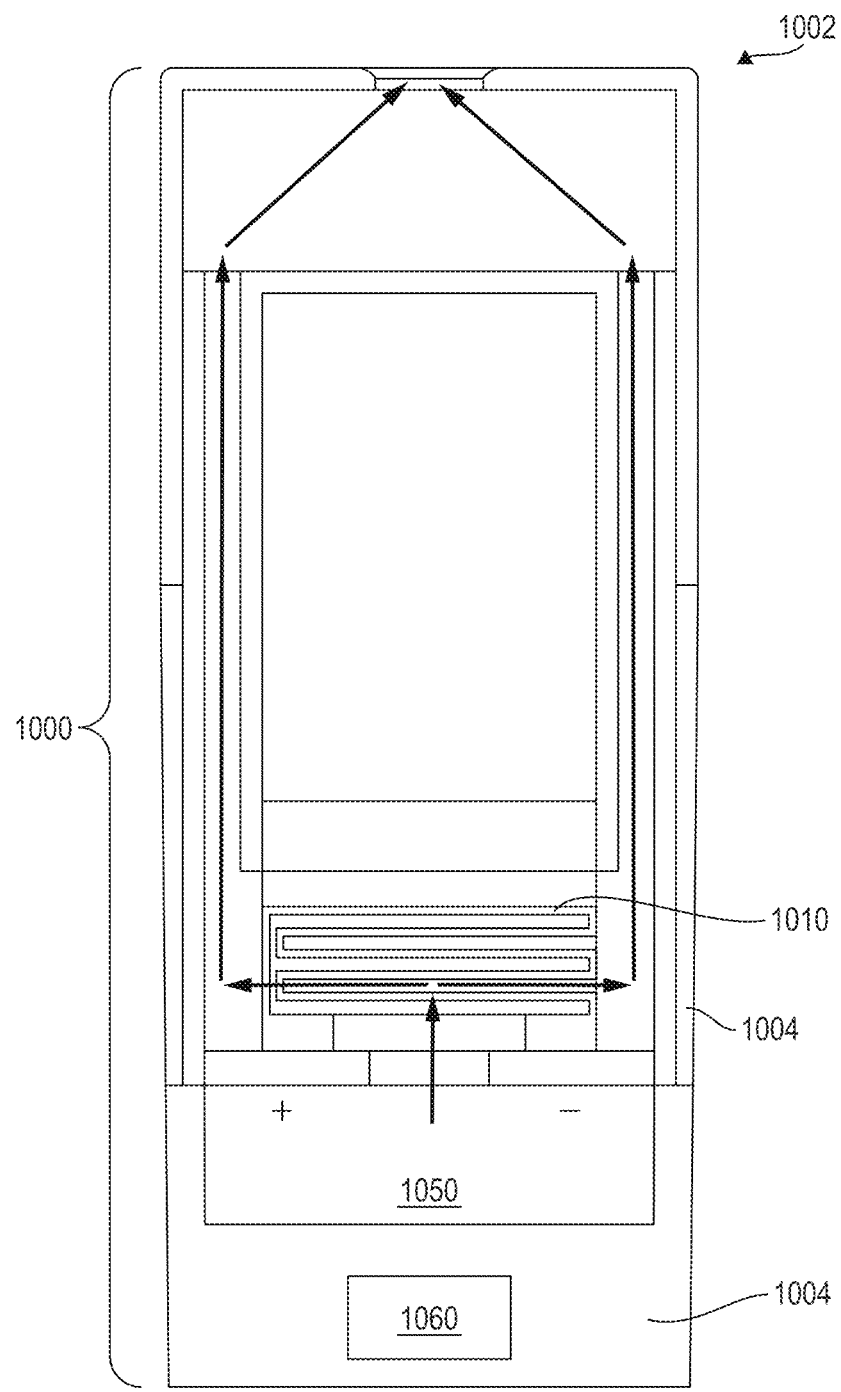
FIG. 10 is partial cross-sectional front view of one exemplary embodiment of a vaporizer device that includes a cartridge integrated into a vaporizer body consistent with implementations of the current subject matter.

FIG. 10 illustrates an exemplary vaporizer device 1000 that includes a cartridge 1002 integrated into a vaporizer body 1004 consistent with implementations of the current subject matter. The cartridge can be similar to the cartridge shown in FIGS. 2A-2B and therefore common elements are not further described herein. In this illustrated embodiment, the vaporizer body 1004 includes a power supply 1050 for connection, via electrical contacts, to the surface heater 1010, and a controller 1060 for various operations, such as heating and puff detection.

Figure 11:
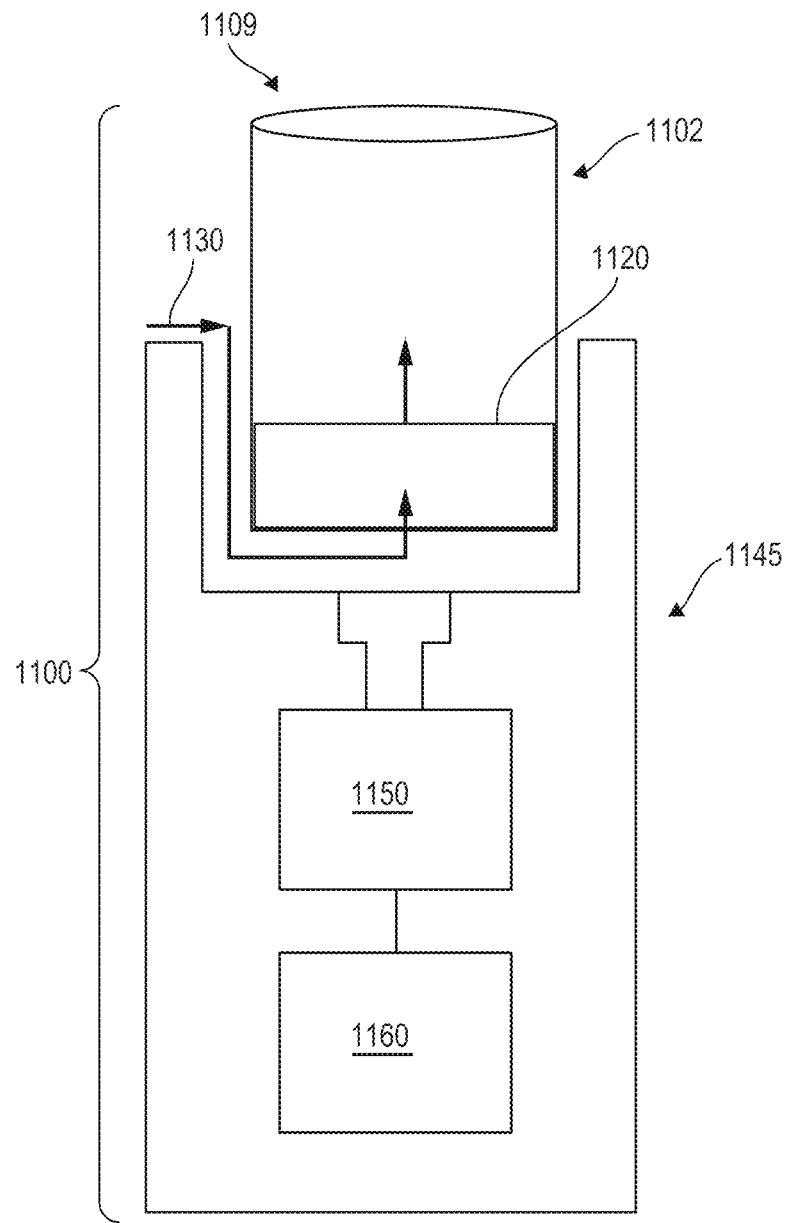
FIG. 11 is a partially transparent perspective view of another exemplary embodiment of a vaporizer device that includes a cartridge coupled to a vaporizer body consistent with implementations of the current subject matter.

FIG. 11 illustrates features of a device 1100 in which a cartridge 1102 (with a porous substrate surface heater 1120 and a mouthpiece 1109) is coupled to a vaporizer body 1145 (with a power supply 1150 and controller 1160). This illustrates how any of the cartridges described herein may couple to and/or be inserted within a vaporizer body. Air flow path 1130 is also illustrated, with the air flow moving over one or more portions of the surface heater 1120.

According to an implementation of the current subject matter, a cartridge may be insertably received into a cartridge receptacle within a vaporizer body to configure a vaporizer device for use. One example of such a configuration is illustrated in FIGS. 13A-13C, in which cartridge 1302 with reservoir 1305 includes a porous substrate 1320, and vaporizer body 1345 includes cartridge receptacle 1304 and surface heater 1310.

Figure 13A:
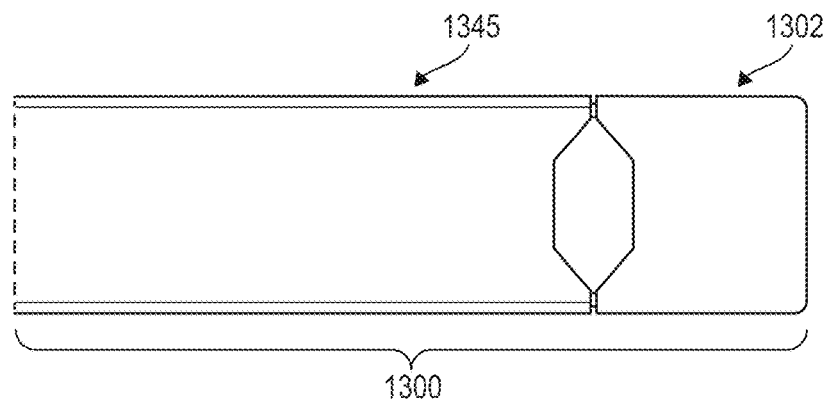
FIG. 13A is a front view of a portion of another exemplary embodiment of a vaporizer device that includes a vaporizer body, a heater integrated into the vaporizer body, and a cartridge having a porous substrate incorporated therein consistent with implementations of the current subject matter, showing the cartridge insertably received into the vaporizer body.

The view in FIG. 13A shows an example of a cartridge 1302 insertably received into a cartridge receptacle within the vaporizer body 1345 to configure the vaporizer device 1300 for use.

Figure 13B:
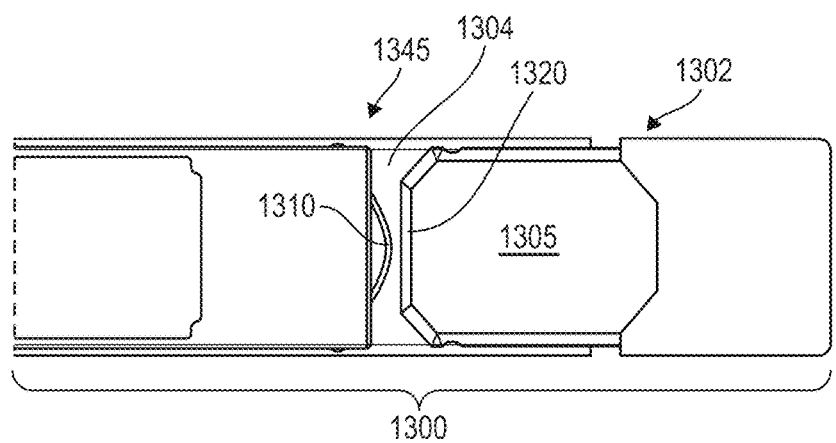
FIG. 13B is a front view of the vaporizer device of FIG. 13A with a front portion of the vaporizer body removed, showing the cartridge being inserted into the vaporizer body.
Figure 13C:
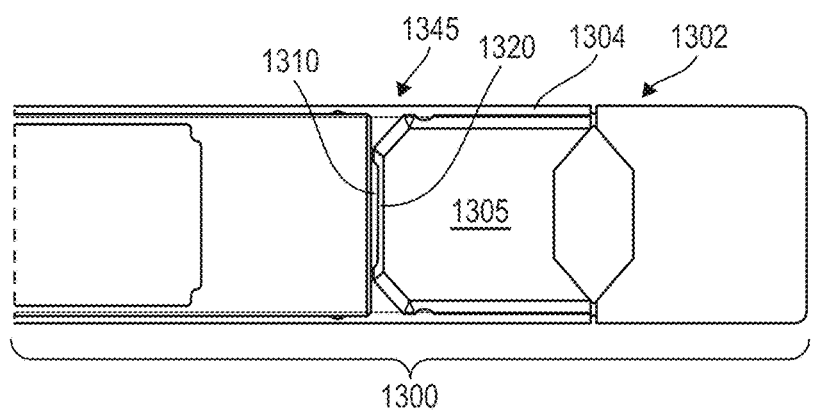
FIG. 13C is a front view of the vaporizer device of FIG. 13A with a front portion of the vaporizer body removed, showing the cartridge insertably received into the vaporizer body.

FIGS. 13B and 13C illustrate features of an exemplary vaporizer device 1300 consistent with implementations of the current subject matter. A vaporizer device 1300 may include a vaporizer body 1345 and a cartridge 1302. The vaporizer body 1345 may include a cartridge receptacle 1304 configured to mechanically connect the vaporizer body 1345 with the cartridge 1302. The cartridge 1302 may generally include a reservoir (or tank) 1305, an air path, and a porous substrate 1320 in accordance with implementations of the current subject matter. The vaporizer body 1345 may include a surface heater 1310 configured to couple with the porous substrate 1320 thereby creating a heated surface portion when cartridge 1302 is insertably received into the cartridge receptacle 1304.

In some implementations, the cartridge may have one or more surfaces of the porous substrate (wick) exposed at the receiving end of the cartridge. The surface heater may be exposed such that the surface heater couples with the wick when the cartridge is inserted into the cartridge receptacle. The surface heater may be configured such that it is flexible and bends from an upward arc into a flat or substantially flat surface to provide additional tension/contact between the wick and the surface heater. An example of such a configuration is shown in FIG. 13C, in which the porous substrate 1320 coupled with the surface heater 1310 is illustrated.

Various features of the above-described implementations of the current subject matter may be combined. For example, an atomizer component in accordance with implementations of the current subject matter may have some features of various ones of the above-described implementations.

An atomizer component in accordance with implementations of the current subject matter may result in improved aerosol production properties relative to a traditional wick, for example one formed of silica fiberglass cord, by maintaining more liquid per unit volume in close proximity to the evaporation surface due to the porosity of the porous substrate and the shape of the porous substrate.

An atomizer component consistent with implementations of the current subject matter may have increased liquid-carrying capacity while also being thermally stable and having sufficient structural integrity for its use in vaporizer devices. Additionally, the porous substrate according to implementations described herein is a robust, easily automatable manufacturable design. In particular, allowing electrical traces to be directly printed in one fashion or another onto the vaporization surface of the porous substrate eliminates the need for manufacturing and embedding or attaching a separate electrical element to the substrate.

The flat surface sides of the porous substrate described herein in accordance with some implementations provide for the heated surface to be easily controlled. The flat design allows for controlling heat zones and the size of the surface heater (e.g., an electrically conductive trace pattern), by for example tuning the exact pattern of the electrical heater traces in different regions. Additionally, the flat surface sides have an increased surface area over traditional round wicks.

Moreover, the use of electrically conductive materials for the surface heater (e.g., in the form of a trace pattern) allows for controlling a temperature of the surface heater using a thermal coefficient of resistance (TCR) based correlation. Different electrically conductive materials (e.g., nickel) can be chosen and utilized to achieve a more stable TCR, resulting in precise temperature sensing/controlling.

Figure 12:
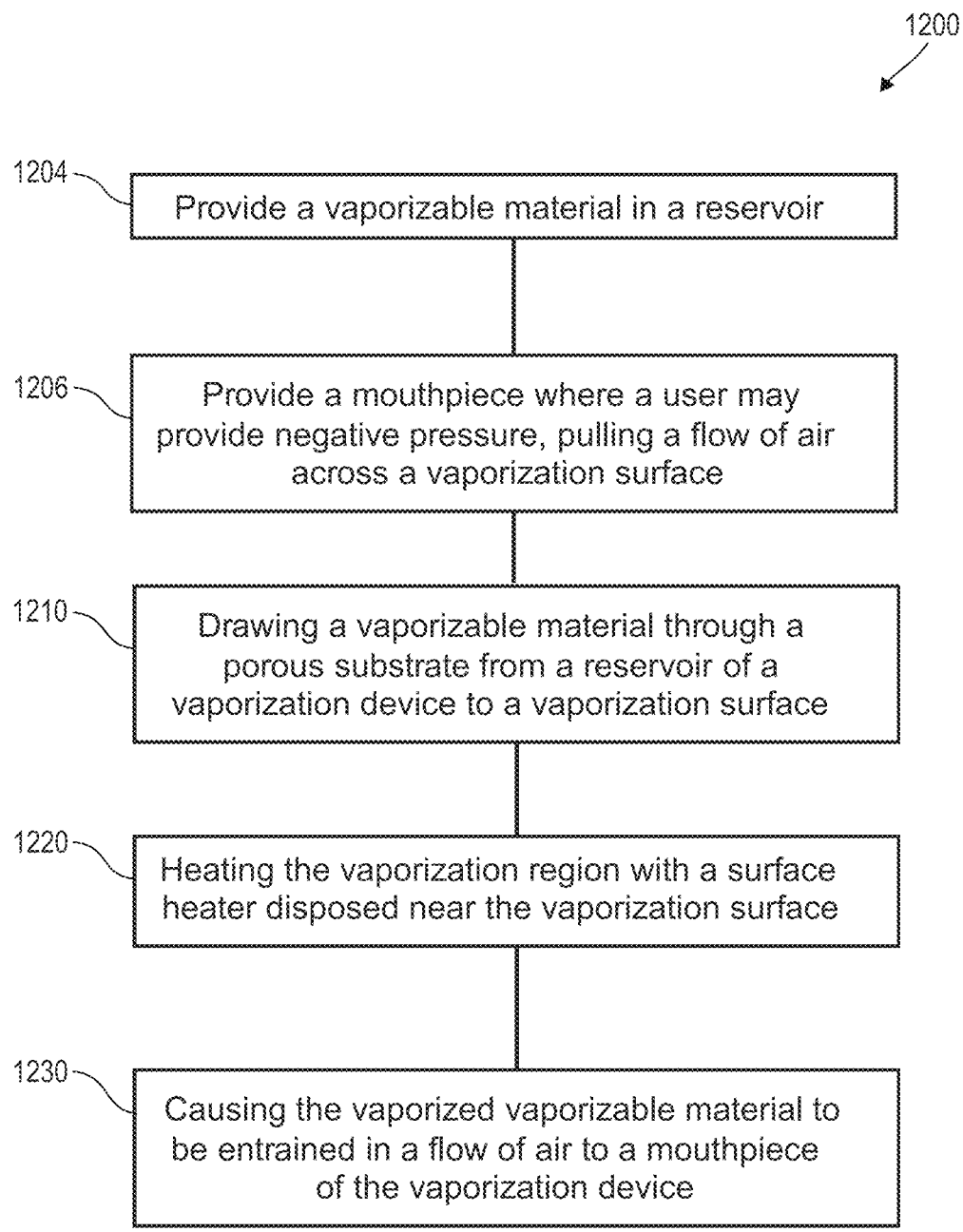
FIG. 12 shows a process flow chart illustrating one exemplary embodiment of a method of drawing a vaporizable material and causing vaporization of the vaporizable material in a vaporization device consistent with implementations of the current subject matter.

With reference to FIG. 12, a process flow chart 1200 illustrates features of a method, which may optionally include some or all of the following. At 1204, a vaporizable material is provided in a reservoir of a vaporization device. At 1206, a mouthpiece where a user may provide negative pressure, pulling a flow of air across a vaporization surface is provided. At 1210, a vaporizable material is drawn, through a porous substrate, from a tank of a vaporization device to a vaporization surface, which includes the heated surface of the porous substrate on which a surface heater is situated. At 1220, the vaporization surface is heated with the surface heater disposed near the vaporization surface. The heating causes vaporization of the vaporizable material in the vaporization surface. At 1230, the vaporized vaporizable material is entrained in a flow of air to a mouthpiece of the vaporization device.

The following is a brief description of certain aspects of the invention, which are not intended to be limiting.

In some aspects, a cartridge for a vaporizer device includes a mouthpiece, a reservoir configured to hold a vaporizable material, and an atomizer component. The atomizer component includes a porous substrate configured to draw the vaporizable material from the reservoir to a vaporization surface exposed to an air flow path, the porous substrate having a rigid, non-deformable form, and a surface heater configured to heat the vaporizable material, the surface heater including at least one electrically conductive layer deposited on a portion of the porous substrate, the vaporization surface including the portion of the porous substrate.

According to some aspects, a vaporization device includes a reservoir configured to hold a vaporizable material, and an atomizer component. The atomizer component includes a porous substrate configured to draw the vaporizable material from the reservoir to a vaporization surface exposed to an air flow path, the porous substrate having a rigid, non-deformable form, and a surface heater configured to heat the vaporizable material, the surface heater including at least one electrically conductive layer deposited on a portion of the porous substrate, the vaporization surface including the portion of the porous substrate.

In some aspects, a method includes drawing, through a porous substrate, a vaporizable material from a reservoir of a vaporization device to a vaporization surface, the porous substrate having a rigid, non-deformable form on at least a portion of which a surface heater including at least one electrically conductive layer is deposited, where the porous substrate is in direct fluid communication with at least a portion of the reservoir, and further where the surface heater is not in direct fluid communication with the reservoir and is directly along an air flow path; heating the vaporization surface with the surface heater to cause vaporization of the vaporizable material; and causing the vaporized vaporizable material to be entrained in a flow of air along the air flow path to a mouthpiece of the vaporization device.

In some aspects, an atomizer component includes a porous substrate configured to draw a vaporizable material from a reservoir, the porous substrate having a rigid, non-deformable form, and a surface heater configured to heat the vaporizable material, the surface heater including at least one electrically conductive layer deposited on a portion of the porous substrate.

According to some aspects, the porous substrate is at least partially contained within the reservoir.

According to some aspects, the porous substrate is fully contained within the reservoir, and the surface heater is positioned away from the vaporizable material in the reservoir.

According to some aspects, the porous substrate is in fluid communication with the reservoir on surfaces other than the portion on which the surface heater is deposited.

In some aspects, an air inlet passage is configured to direct a flow of air along the vaporization surface in the air flow path such that when the surface heater is activated, the vaporizable material drawn by the porous substrate along the vaporization surface is evaporated into the flow of air.

According to some aspects, the at least one electrically conductive layer includes a trace pattern or a plate.

According to some aspects, the at least one electrically conductive layer includes a micro-electrical-mechanical systems (MEMS) layer.

According to some aspects, the at least one electrically conductive layer allows for the vaporizable material from the reservoir to pass therethrough.

In some aspects, the at least one electrically conductive layer further includes one or more electrical contacts for interfacing with one or more respective pins. The one or more electrical contacts may be deposited on a surface of the porous substrate on which a remaining portion of the at least one electrically conductive layer is not deposited.

In some aspects, the mouthpiece is disposed at a first end of a body of the cartridge and the heating element is disposed at a second end of the body, opposite the first end.

In some aspects, the porous substrate includes a plurality of voids dispersed throughout the porous substrate.

In some aspects, the porous substrate includes a stacked configuration formed of a plurality of separate substrates stacked one on top of another.

According to some aspects, at least a portion of the surface heater is disposed between two of the plurality of the separate substrates.

According to some aspects, the portion of the porous substrate on which the electrically conductive layer is deposited includes a planar surface, a concave surface, or a cylindrical surface.

As mentioned above, traditional vaporizer devices have used an atomizer that includes a wicking element (or wick) that draws an amount of vaporizable material from the reservoir (reservoir chamber) to a part of the atomizer that includes a heating element (e.g., conductive, convective, and/or radiative). Generally, in such instances, the heating element is in thermal communication with the wicking element, which is at least partially disposed within the reservoir chamber containing a bulk amount of vaporizable material. As a result, when the wicking element is heated so as to vaporize at least a portion of the vaporizable material contained therein, an amount of heat is lost to the bulk amount of vaporizable material. Therefore, to ensure a sufficient amount of vaporizable material within the wicking element is vaporized, excess energy is supplied by the heating element. Further, due to the lack of thermal insulation of the atomizer, additional thermal loses can be incurred, thereby requiring additional excess energy to be supplied. This lack of thermal insulation can also result in at least a portion of the supplied energy dissipating to other areas of the vaporizer devices, which can lead to loss in structural integrity of the device, damage to internal components, etc. Moreover, due to the microstructure of the wicking element, it can also be difficult to control the amount and rate at which the vaporizable material is being drawn therein. Various features and devices are described below that improve upon or overcome these issues. For example, various features are described herein that allow for a more controlled delivery of vaporizable material to the heating area of the vaporizer devices, which may provide advantages and improvements relative to existing approaches, while also introducing additional benefits as described herein.

In some aspects, the vaporizer cartridges described herein utilize an atomizer that is in fluid communication with a reservoir chamber that is configured to selectively hold a vaporizable material. The atomizer includes a substrate having a channel extending at least partially therethrough that may allow for a more controlled delivery of vaporizable material to the heating area of the vaporizer device. As an example, the structural dimensions of the channel (e.g., diameter, length, or the like) may be tailored to control the amount of and/or the rate at which vaporizable material is received into the atomizer (e.g., from a reservoir chamber that contains a bulk amount of vaporizable material) for subsequent vaporization. As such, the channel may be configured to receive a predetermined volume of vaporizable material, e.g., from a reservoir chamber, at a predetermined rate. The atomizer also includes at least one surface heater that is configured to selectively heat at least a portion of the vaporizable material received within the channel into a vaporized vaporizable material. The at least one surface heater may provide a smaller, defined heating area for vaporizable material. As discussed in greater detail below, the atomizer allows for vaporizable material to be withdrawn therein, and thus, separated from the remaining bulk amount of vaporizable material. This may avoid unnecessary heating of bulk vaporizable material when vaporizing the vaporizable material within the atomizer. As a result, thermal efficiency may be optimized.

The substrate may have a variety of configurations. In some aspects, for example, the substrate may have at least two spaced apart surfaces that each define a boundary of the channel. In such aspects, the channel is open-ended, and therefore extends completely through the thickness or depth of the substrate. For example, the substrate may include first and second sidewalls that are spaced apart from one another in a first direction, in which the first and second sidewalls each extend from an inner surface to an outer surface. The inner surface of the first sidewall and the inner surface of the second sidewall each define a boundary of the channel. The substrate may also include third and fourth sidewalls that are spaced apart from one another in a second direction that is opposite the first direction, in which the third and fourth sidewalls each extend from an inner surface to an outer surface. The inner surface of the third sidewall and the inner surface of the fourth sidewall each define a boundary of the channel.

The size and shape of the channel may be dependent at least upon the structural dimensions of the substrate. For example, two or more spaced apart surfaces of the at least two spaced apart surfaces (e.g., the inner surfaces of the first and second sidewalls or the inner surfaces of the third and fourth sidewalls) may optionally be parallel or at least approximately parallel. In certain aspects, one or more of the two or more spaced apart surfaces may optionally be at least approximately planar. In other aspects, one or more of the two or more spaced apart surfaces may be curved, undulating, ridged, or otherwise be non-planar on at least some of the surface. A person skilled in the art will appreciate that the amount and/or rate at which at which vaporizable material is received within the channel may be dependent at least upon the distance between and the lengths of the at least two spaced apart surfaces. As such, the predetermined volume of the vaporizable material may enter the channel via capillary pressure and/or gravity.

In some instances where capillary pressure created within the channel draws vaporizable material therein, the channel can have a diameter that is equal to the distance between the at least two spaced apart surfaces, and/or a length that is equal to the length of one or more of the at least two spaced apart surfaces. In other instances where capillary pressure draws vaporizable material into the channel, the channel can have a diameter that is less than the distance between the at least two spaced apart surfaces, and/or a length that is less than the length of one or more of the at least two spaced apart surfaces.

The substrate may further include a base that extends between the at least two spaced apart surfaces. The base may have a variety of configurations. In general, the base extends from a first surface (e.g., inner surface) to a second surface (e.g., outer surface) that is opposite the first surface, in which the first surface further defines the boundary of the channel. In such aspects, the channel is closed-ended and therefore partially extends through the thickness or depth of the substrate. The size and shape of the base may be dependent at least upon the structural dimensions of the at least two spaced apart surfaces and the distance therebetween. For example, in various aspects, the first and second surfaces may optionally be parallel or at least approximately parallel. In other aspects, the first and second surfaces may have other relative orientations. In certain aspects, one or both of the first and second surfaces may optionally be at least approximately planar. In other aspects, either or both of the first and second surface may be curved, undulating, ridged, or otherwise be non-planar on at least some of the surface.

The substrate may be formed from any suitable materials (s). In some aspects, the substrate is formed of one material, whereas in other embodiments, the substrate is formed of two or more materials. For example, the substrate may include first and second sidewalls each formed of one material (e.g., an electrically conducting material) and a base formed of another material (e.g., an electrically conducting material). In some aspects, the substrate can be formed as a unitary structure.

In some aspects, the substrate may include at least one vent extending from a first surface of the substrate to a second surface of the substrate, the second surface being opposite of the first surface. That is, the at least one vent extends completely through the thickness or depth of the substrate. The at least one vent may be configured to allow the passage of air into the reservoir chamber in response to the withdrawal of at least a portion of the vaporizable material from the reservoir chamber and into the channel of the substrate. This influx of air can help stabilize a hydrostatic offset that can be created within the cartridge when the vaporizable material is drawn into the porous substrate.

The at least one vent may have a variety of configurations. In some aspects, the at least one vent may have a varying cross-sectional area, whereas in other aspects, the at least one vent may have a constant cross-sectional area. For example, the at least one vent may have a first portion with a first cross-sectional area and a second portion with a second cross-sectional area that is less than the first cross-sectional area. In some aspects, the first portion can be proximate to the reservoir chamber and the second portion is distal to the reservoir chamber.

In some aspects, the at least one surface heater may be positioned and therefore extend across two different portions of the substrate. In other aspects, the at least one surface heater may include a first surface heater positioned on a first portion of the substrate, and a second surface heater positioned on a second portion of the substrate. For example, the first surface heater may be positioned on the outer surface of the first sidewall of the substrate and the second surface heater may be positioned on the outer surface of the second sidewall of the substrate. In some aspects, the first surface heater and the second surface heater may be electrically separated from each other (e.g., not in electrical communication). In other embodiments, the first surface heater and second surface heater are electrically bridged together (e.g., in electrical communication).

The at least one surface heater may have a variety of configurations. For example, in some aspect, the at least one surface heater may include at least one electrically conductive layer on or in contact with at least a portion of the substrate. The at least one electrically conductive layer may include a trace pattern deposited on at least one surface or at least a portion of the at least one surface of the substrate (e.g., the outer surface of either the first or second sidewall, the outer surface of both the first and second sidewalls, or the outer surface of both the first and second sidewall and the second surface of the base). A trace pattern may be configured to achieve a desired and controlled electrical resistance, and may or may not be uniform in thickness or extent along the surface of the substrate. Specific shapes, patterns, thickness, etc. of the surface heater may be advantageous in allowing control of heat delivery to the substrate to be controlled. Alternatively, the at least one electrically conductive layer may be a plate or other continuous layer that covers at least one entire surface of the substrate (e.g., the outer surface of either the first or second sidewall, the outer surface of both the first and second sidewalls, or the outer surface of both the first and second sidewall and the second surface of the base). The at least one electrically conductive layer may be made from any electrically conductive material, such as, for example and without limitation, a nickel chromium alloy, stainless steel, nickel, platinum, gold, copper, or aluminum. The at least one electrically conductive layer may be a micro-electrical-mechanical systems (MEMS) layer. In this manner, or in other approaches consistent with the current subject matter, at least one surface heater may be in contact with at least a portion of a surface of the substrate.

The at least one surface heater may be adhered to the porous substrate in a number of ways, such as by pulsed laser deposition, physical vapor deposition, chemical vapor deposition, electroplating, electro-less plating, screen printing, or the like. In some variations of the current subject matter, the at least one surface heater may be a stamped part that is snapped onto or otherwise mechanically retained by the substrate. In other variations, the at least one surface heater may be a stamped part that is insert molded into the substrate. In other variations, the at least one surface heater is fixed to the porous substrate by any secure attachment method.

The at least one surface heater may have areas of lower electrical resistance that may be used as contacts for electrically interfacing the cartridge with a vaporizer body (e.g., connection with contact pins of the vaporizer body (e.g., pogo pins or leaf spring pins of a vaporizer body)).

Figure 14:
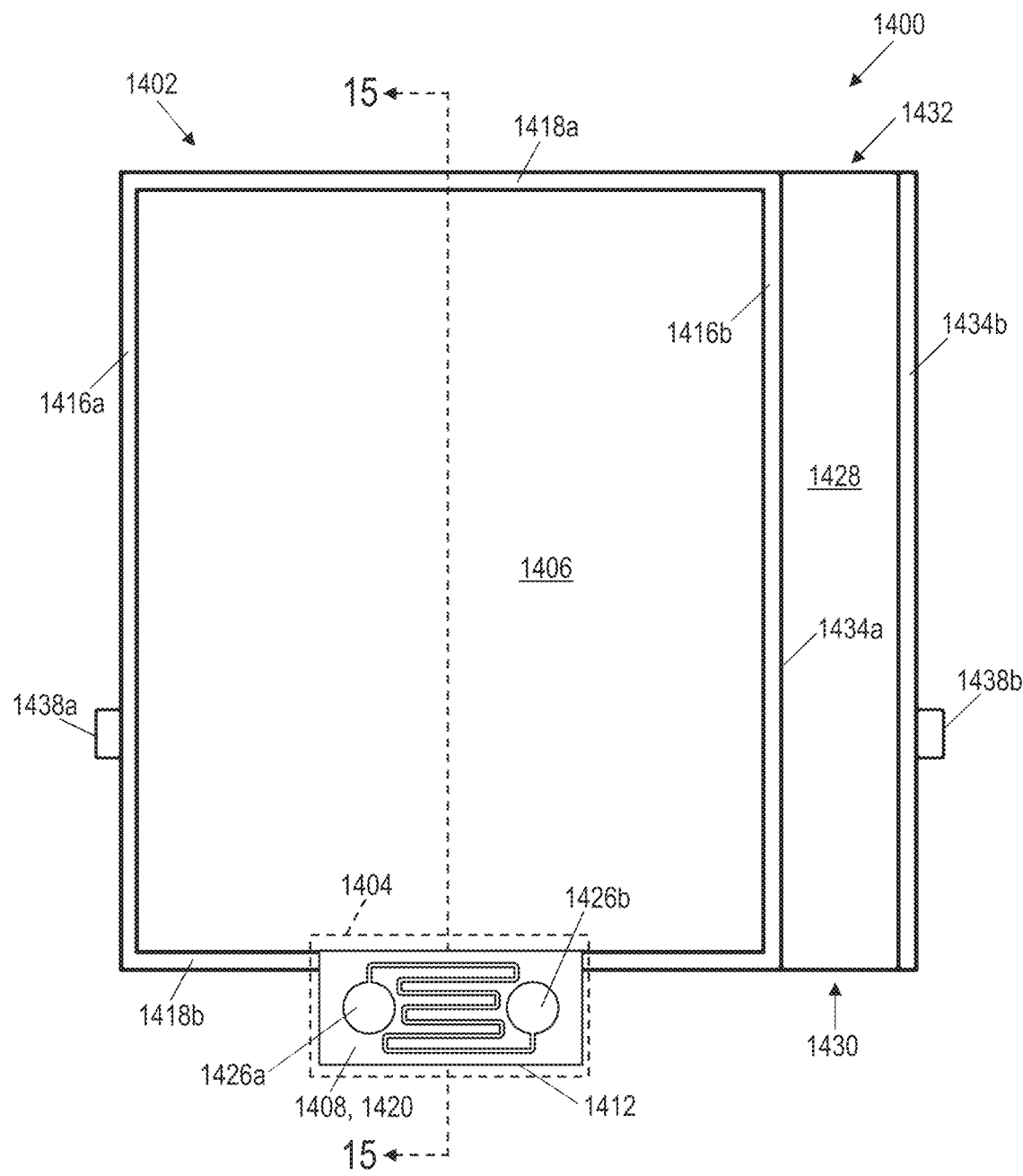
FIG. 14 is a cross-sectional front view of another exemplary embodiment of a cartridge for use in a vaporizer device consistent with implementations of the current subject matter, the cartridge having a reservoir and an atomizer that includes a substrate having a channel defined therethrough and at least one surface heater.
Figure 15:
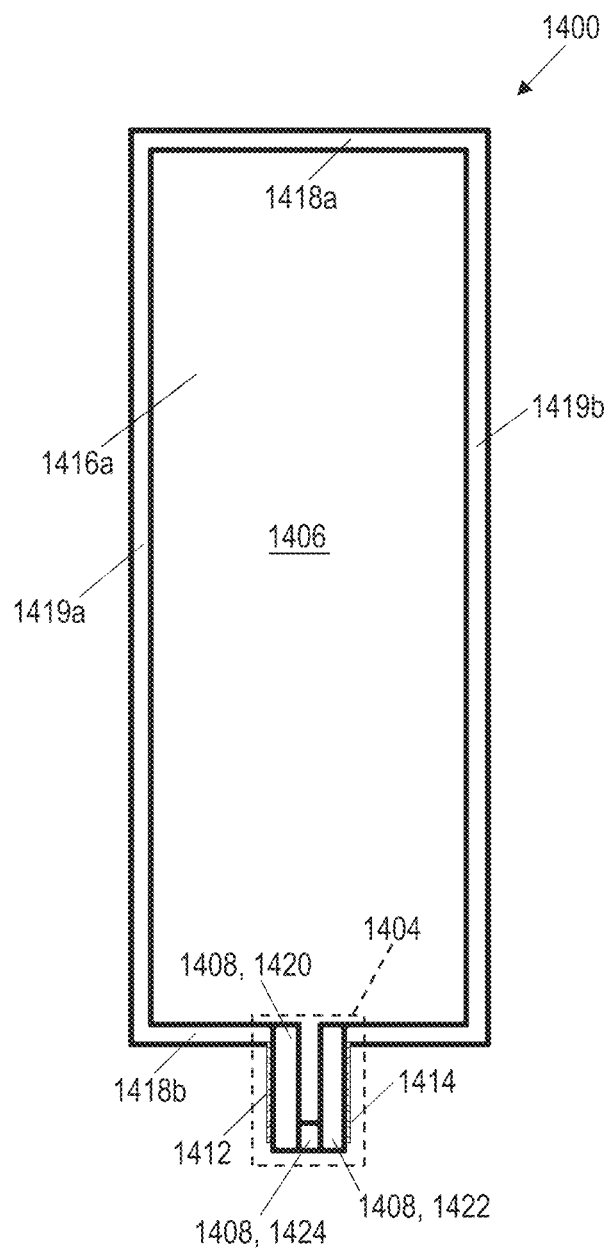
FIG. 15 is a cross-sectional side view of the cartridge of FIG. 14 taken at 15-15.
Figure 16:
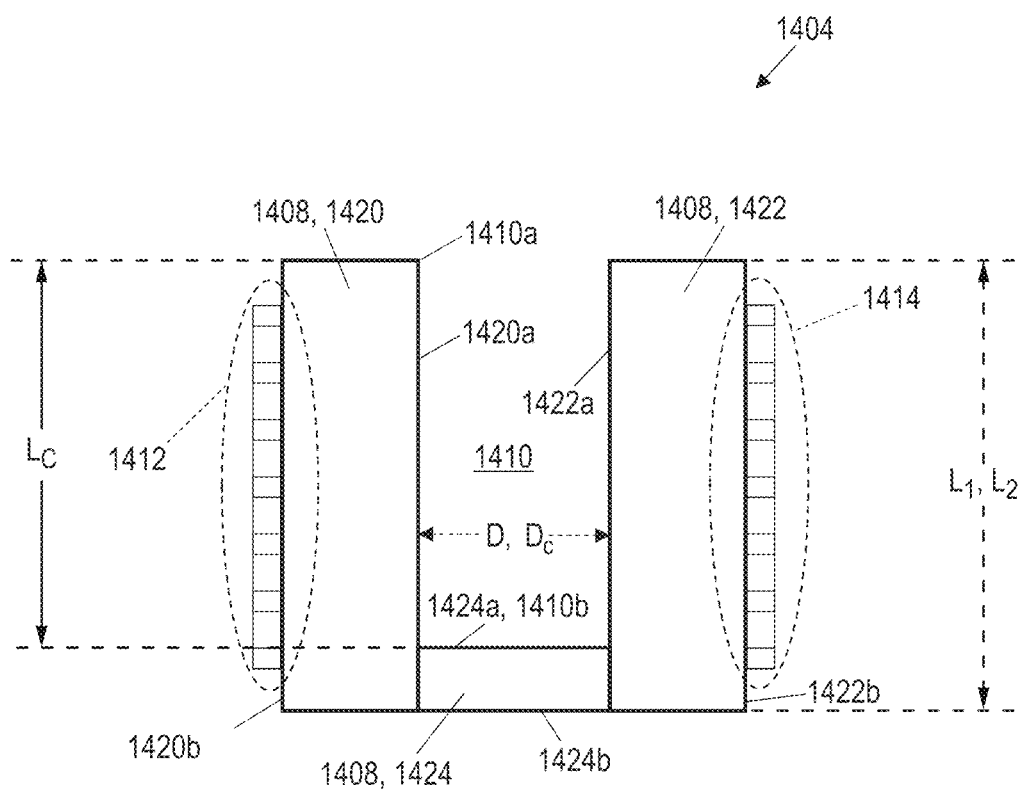
FIG. 16 is a magnified cross-sectional view of the atomizer of FIG. 15.

FIGS. 14 and 15 illustrate an exemplary cartridge 1400 for a vaporizer device. More specifically, the cartridge 1400 includes a reservoir housing 1402 and an atomizer 1404 that is in fluid communication with a reservoir chamber 1406. The atomizer 1404, as shown in FIGS. 14-16, includes a substrate 1408 having a channel 1410 extending partially therethrough, and first and second surface heaters 1412, 1414. For purposes of simplicity only, certain components of the cartridge 1400 are not illustrated.

The reservoir housing 1402 includes the reservoir chamber 1406. The reservoir chamber 1406 is configured to hold a vaporizable material (not shown). While the reservoir housing 1402 can have a variety of sizes and shapes, the reservoir housing 1402, as shown in FIGS. 14 and 15, is substantially rectangularly shaped. The reservoir housing 1402 includes at least two sets of opposing sidewalls in which the first set of opposing sidewalls 1416a, 1416b extends substantially perpendicular to the second set of opposing sidewalls 1418a, 1418b. As shown, these sidewalls 1416a, 1416b, 1418a, 1418b define at least a portion of the reservoir chamber 1406. Further, as shown in FIG. 15, the reservoir housing includes a third set of opposing sidewalls 1419a, 1419b that extends substantially perpendicular to the first and second sets of opposing sidewalls 1416a, 1416b, 1418a, 1418b.

While the substrate 1408 can have a variety of configurations, the substrate 1408, as shown in FIGS. 14-16, include first and second opposing sidewalls 1420, 1422 and a base 1424 extending therebetween. The first and second opposing sidewalls 1420, 1422 are spaced apart from each other at a distance (D). While the first and second opposing sidewalls 1420, 1422 and the base 1424 can have a variety of shapes and sizes, as shown, the two opposing sidewalls 1420, 1422 and the base 1424 are each substantially rectangularly shaped. As further shown in FIG. 16, the first and second opposing sidewalls 1420, 1422 each extend from an inner surface 1420a, 1422a to an outer surface 1420b, 1422b, and the base 1424 extends from an inner surface 1424a to an outer surface 1424b. The inner surfaces 1420a, 1422a, 1424a define the boundary of the channel 1410 extending partially through the substrate 1408. As a result, in this illustrated embodiment, a first end 1410a of the channel 1410 is open, and in fluid communication with the reservoir chamber 1406, and a second end 1410b of the channel is closed. Further, in this illustrated embodiment, the second end 1410b is defined by the inner surface 1424a of the base 1424.

In use, the channel 1410 receives at least a portion of the vaporizable material (not shown) from the reservoir chamber 1406 through its first end 1410a towards its second end 1410b. As discussed above, the structural dimensions (diameter and length) of the channel 1410 can control the amount and/or flow rate of the vaporizable material from the reservoir chamber 1406 and into the atomizer 1404. In this illustrated embodiment, the diameter ($D_c$) of the channel 1410 is equal to the distance (D) between the first and second opposing sidewalls 1420, 1422, and the length ($L_c$) of the channel 1410 is less than the length ($L_1$, $L_2$) of the first and second opposing sidewalls 1420. As a result, the amount and/or rate at which the vaporizable material is received within the channel 1410 is dependent at least upon the distance (D) between and the lengths ($L_1$, $L_2$) of the first and second opposing sidewalls 1420, 1422 of the substrate 1408. Thus, depending on at least this distance (D) and lengths ($L_1$, $L_2$), the predetermined volume of the vaporizable material may enter the channel 1410 via capillary pressure and/or gravity for vaporization by the first surface heater 1412 and/or the surface heater 1414.

While the first and second surface heaters 1412, 1414 can each have a variety of configurations, as shown in FIGS. 14-16, the first and second surface heaters 1412, 1414 each include an electrically conductive layer having a trace pattern. As shown, the first surface heater 1412 is deposited on a portion of the outer surface 1420b of the first opposing sidewall 1420 and the second surface heater 1414 is deposited on a portion of the outer surface 1422b of the second opposing sidewall 1422. Further, as shown in FIG. 14, two electrical contacts 1426a, 1426b are positioned at opposite ends of the trace pattern of the electrical conductive layer of the first surface heater 1412. While not shown, two electrical contacts are also positioned at opposite ends of the trace pattern of the electrical conductive layer of the second surface heater 1414. Each of the electrical contacts are sized and shaped for connection with contact pins (e.g., pogo pins or leaf spring pins) of a vaporizer body, like vaporizer body 1702 shown in FIGS. 17 and 18, for operation. In use, the first surface heater 1412 and/or the second surface heater 1414 is activated to generate heat so as to vaporize at least a portion of the vaporizable material that is within the channel 1410, and thus the substrate 1408, into vaporized vaporizable material.

As further shown in FIG. 14, the cartridge 1400 also includes an internal channel 1428 that extends from an inlet 1430 to an outlet 1432 of the cartridge 1400. The internal channel 1428 is configured to direct air and vaporized vaporizable material through the cartridge 1400 for inhalation by a user. While the internal channel 1428 can have a variety of configurations, the internal channel 1428, as shown in FIG. 15, is defined by at least first and second opposing sidewalls 1434a, 1434b. Further, in this illustrated embodiment, the sidewall 1416b of the reservoir housing 1402 and the first sidewall 1434a of the internal channel 1428 are the same. In other embodiments, the internal channel 1428 can be sized and shaped differently, including any other possible shape.

Figure 17:
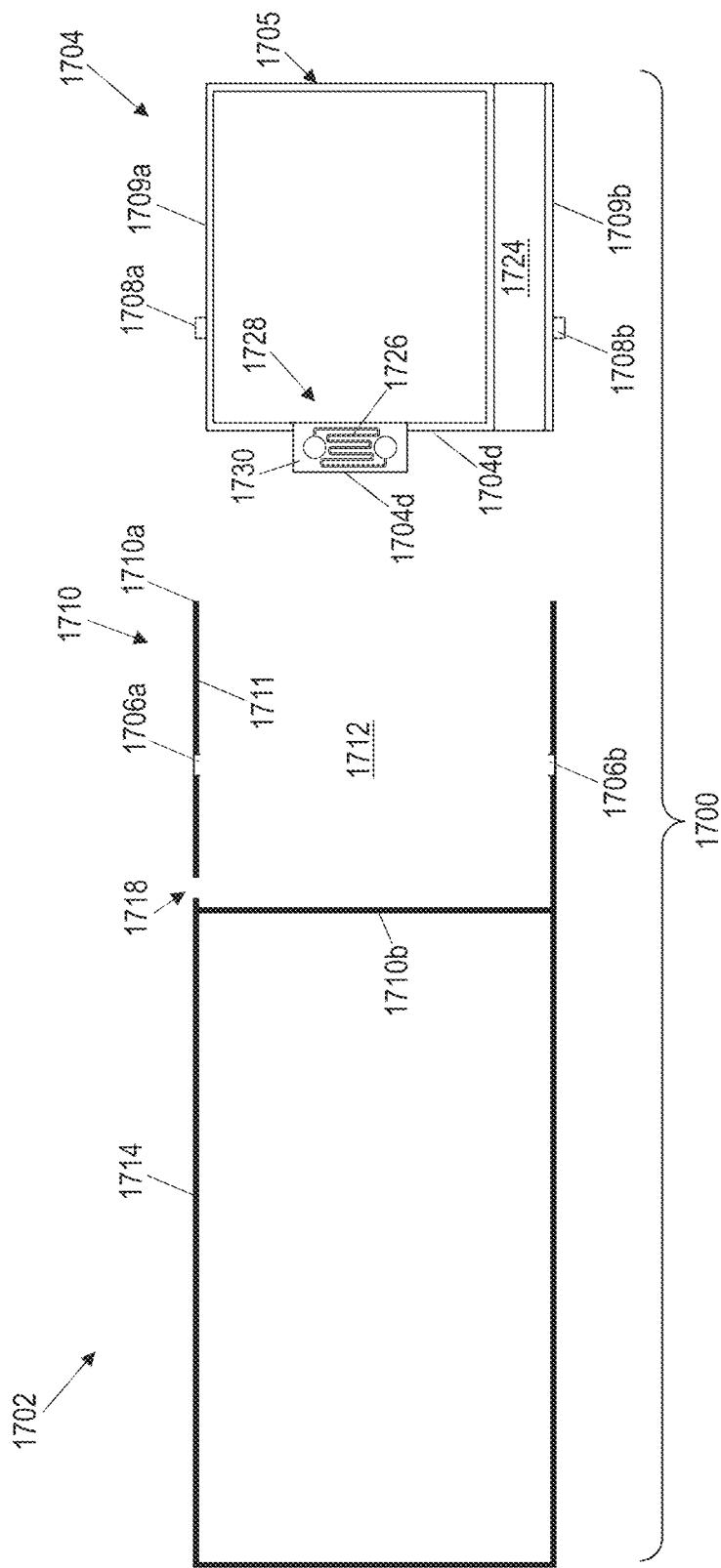
FIG. 17 is a partially transparent top view of another exemplary embodiment of a vaporizer device that includes a vaporizer body and a cartridge having a reservoir chamber and an atomizer consistent with implementations of the current subject matter, showing the vaporizer body and cartridge separated from each other.
Figure 18:
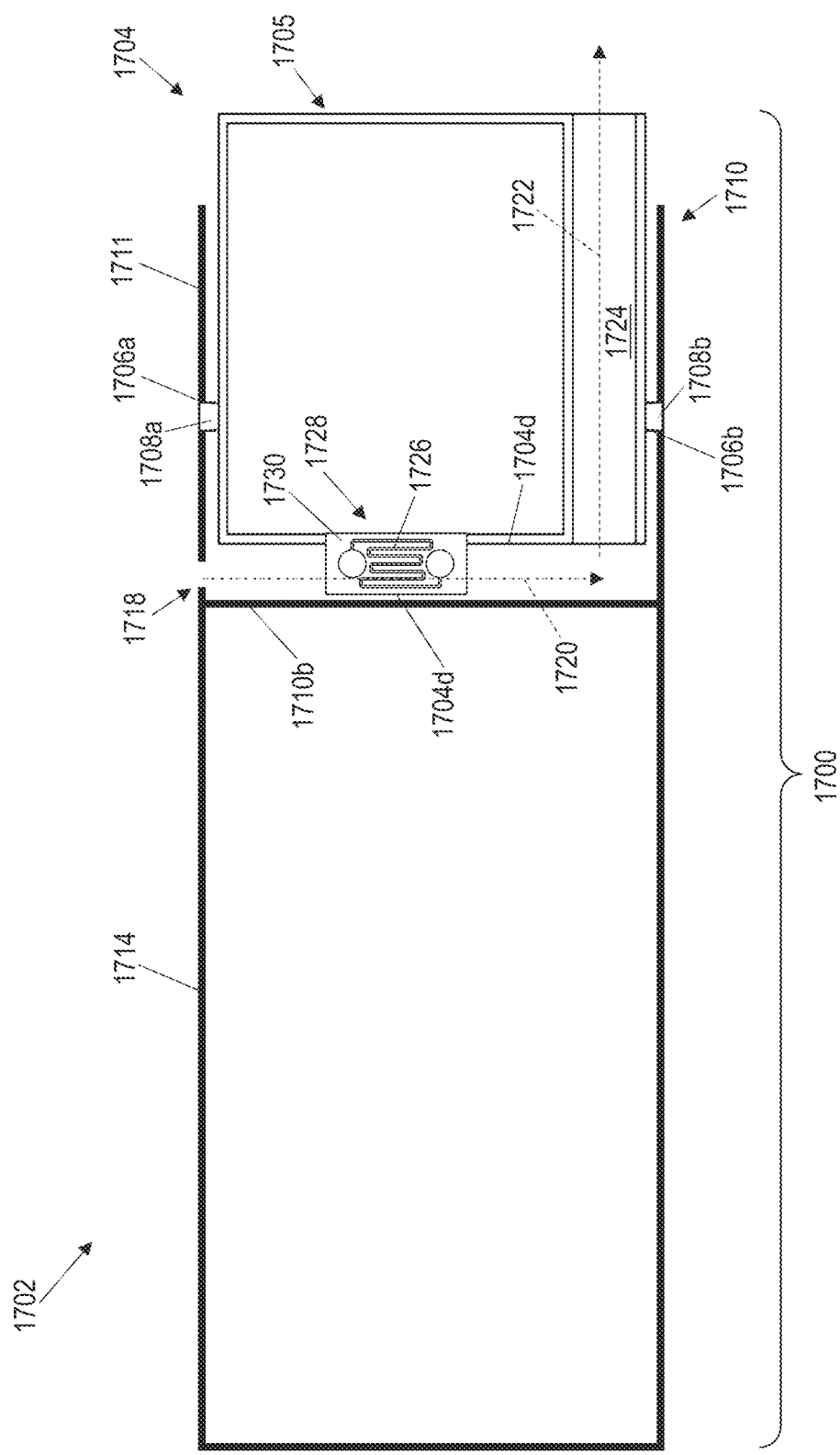
FIG. 18 is a partially transparent top view of the vaporizer device of FIG. 17, showing the cartridge inserted into a cartridge receptacle of the vaporizer body.

Further, as shown in FIG. 14, the cartridge 1400 also includes a set of coupling elements 1438a, 1438b that can be used to selectively couple the cartridge 1400 to a vaporizer body, such as vaporizer body 1702 shown in FIGS. 17 and 18. While the set of coupling elements 1438a, 1438b can have a variety of configurations, in this illustrated embodiment, each coupling element 1438a, 1438b includes a protrusion extending outwardly from a sidewall of the cartridge 1400. In particular, the protrusion of the first coupling element 1438a extends from the sidewall 1416a of the reservoir housing 1402 and the protrusion of the second coupling element 1438b extends from the second sidewall 1434b of the internal channel 1428 of the cartridge 1400. In other embodiments, the set of coupling elements 1438a, 1438b can have any other suitable configurations that can be used to selectively couple to corresponding features (e.g., channels, troughs, holes, hooks, grooves, detents, etc.) in the vaporizer body.

FIGS. 17 and 18 illustrate an exemplary vaporizer device 1700 that includes a vaporizer body 1702 and a cartridge 1704. In FIG. 17, the vaporizer body 1702 and the cartridge 1704 are illustrated in a decoupled configuration, whereas in FIG. 18, the vaporizer body 1702 and the cartridge 1704 are illustrated in a coupled configuration. The cartridge 1704 is similar to cartridge 1400 in FIGS. 14 and 15 is therefore not described in detail herein. For purposes of simplicity, certain components of the vaporizer device 1700 are not illustrated in FIGS. 17 and 18.

The vaporizer body 1702 and the cartridge 1704 can be coupled to each other by way of corresponding coupling elements. For example, as shown in FIGS. 17 and 18, the vaporizer body 1702 includes a first set of coupling elements 1706a, 1706b, and the cartridge 1704 includes a second set of corresponding coupling elements 1708a, 1708b. While the first and second set of coupling elements can have a variety of configurations, in this illustrated embodiment, the first set of coupling elements 1706a, 1706b include two recess pores extending inward into the vaporizer body 1702 and the second set of coupling elements 1708a, 1708b include two protrusions extending outwardly from two opposing sidewalls 1709a, 1709b of the cartridge 1704.

The vaporizer body 1702 can have a variety of configurations. As shown in FIGS. 17 and 18, the vaporizer body 1702 includes a sleeve 1710 that extends from a proximal end 1710a to a distal end 1710b. The sleeve 1710 defines a cartridge receptacle 1712 within the vaporizer body 1702 that is configured to receive at least a portion of the cartridge 1704. The distal end 1710b of the sleeve 1710 is coupled to a chassis 1714 that is configured to house at least a portion of additional components of the vaporizer device 1700, such as, for example, a power source, input device(s), sensor(s), output, a controller, communication hardware, memory, and the like. Once the cartridge 1704 is coupled to the vaporizer body 1702, a first airflow path 1720, as shown in FIG. 18, is created within the cartridge receptacle 1712 between the distal end 1710b of the sleeve 1710 and a distal end 1704d of the cartridge 1704.

Further, as shown in FIGS. 17 and 18, a first air inlet 1718 extends through a wall 1711 of the sleeve 1710. This first air inlet 1718 is configured to allow at least a portion of ambient air outside of the vaporizer body 1702, and thus outside of the reservoir housing 1705 of the cartridge 1704, to enter the vaporizer device 1700. In use, when a user puffs on the device, at least a portion of ambient air enters the vaporizer body 1702 and travels through the first airflow path 1720. As described in more detail below, vaporized vaporizable material joins the first airflow path 1720 and combines with at least a portion of the air to form a mixture. The mixture travels through the remaining portion of the first airflow path 1720 and then through a second airflow path 1722 that extends through an internal channel 1724 of the cartridge 1704. As such, the first and second airflow paths 1720, 1722 are in fluid communication with each other.

In use, once the cartridge 1704 is coupled to the vaporizer body 1702, the first surface heater 1726 and/or the second surface heater (obscured in FIGS. 17 and 18) of the atomizer 1728 can be activated by a user puffing on the cartridge 1704 and at least a portion of vaporizable material within the substrate 1730 of the atomizer 1728 is vaporized into vaporized vaporizable material. This puffing also concurrently draws ambient air into the first airflow path through the first air inlet 1718 of the sleeve 1710. As a result, at least a portion of the vaporized vaporizable material joins the air traveling along the first airflow path 1720. Subsequently, at least a portion of the joined vaporized vaporizable material and air continues to travel through the vaporizer body 1702 and into the second airflow path 1722 of the cartridge 1704. As the joined vaporized vaporizable material and air travel through at least the second airflow path 1722, and thus, the internal channel 1724 of the cartridge 1704, they at least partially condense into aerosol for subsequent inhalation by a user.

As mentioned above, drawing of the vaporizable material from the reservoir chamber can be due, at least in part, to capillary action provided by the porous substrate. However, as vaporizable material is drawn out of the reservoir chamber, the pressure inside the reservoir chamber is reduced, thereby creating a vacuum and acting against the capillary action. This can reduce the effectiveness of the porous substrate to draw the vaporizable material from the reservoir chamber, thereby reducing the effectiveness of the vaporizer to vaporize a desired amount of vaporizable material, such as when a user takes a puff on the vaporizer device. Furthermore, the vacuum created in the reservoir chamber can ultimately result in the inability to draw all of the vaporizable material therefrom, thereby wasting vaporizable material. Various features and devices are described below that improve upon or overcome these issues. For example, various features are described herein for controlling airflow in a vaporizer device, which may provide advantages and improvements relative to existing approaches, while also introducing additional benefits as described herein.

Figure 19:
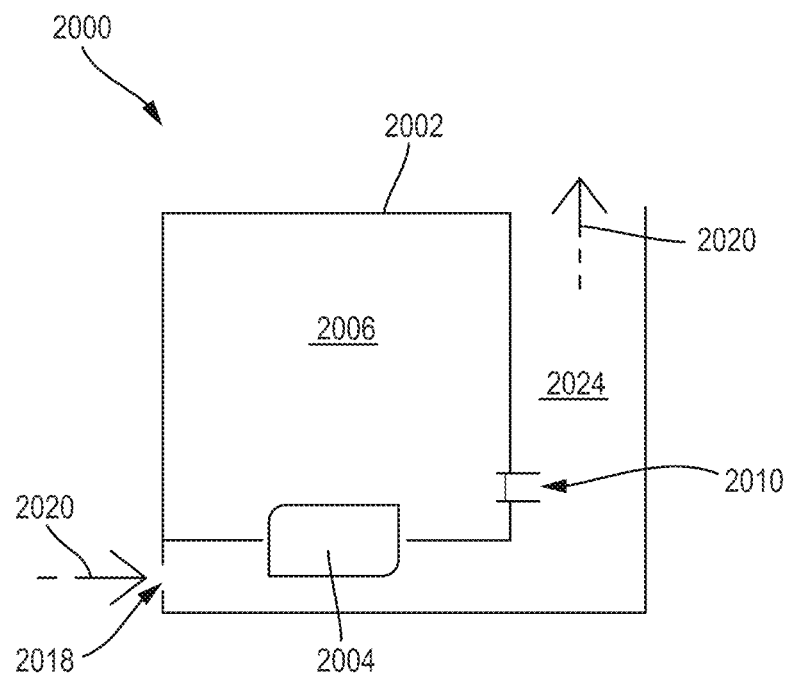
FIG. 19 is a cross-sectional view of an exemplary embodiment of a reservoir system configured for a vaporizer cartridge and/or vaporizer device consistent with the implementations of the current subject matter.
Figure 20:
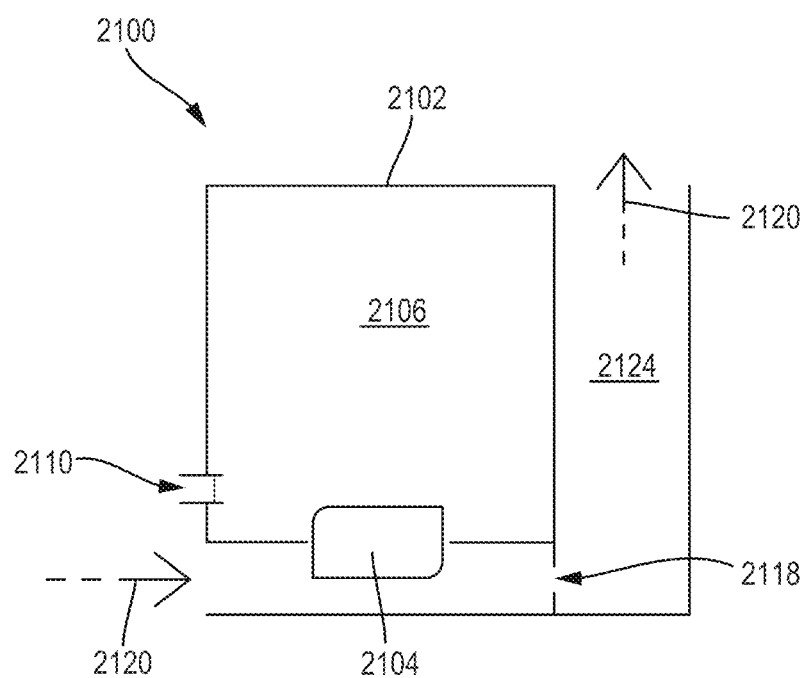
FIG. 20 is a cross-sectional view of another exemplary embodiment of a reservoir system configured for a vaporizer cartridge and/or vaporizer device consistent with the implementations of the current subject matter.

FIGS. 19 and 20 illustrate exemplary first and second embodiments, respectively, of a reservoir system 2000, 2100 configured for a vaporizer cartridge and/or vaporizer device for improving airflow in the vaporizer device. More specifically, the reservoir systems 2000, 2100 illustrated in FIGS. 19 and 20 improve the regulation of pressure within the reservoir chamber 2006, 2106 such that a vacuum created in the reservoir chamber 2006, 2106 is relieved after a user puffs on the vaporizer device. This allows the capillary action of the porous substrate of the atomizer 2104 to continue to effectively draw vaporizable material from the reservoir chamber 2006, 2106 after each puff.

As shown in FIGS. 19 and 20, the reservoir systems 2000, 2100 include a reservoir chamber 2006, 2106 configured to contain a vaporizable material. The reservoir chamber 2006, 2106 is sealed on all sides by reservoir housing walls 2002, 2102 except through a porous substrate of the atomizer 2104. The atomizer 2004, 2104 also includes a surface heater that is deposited on a surface of the porous substrate. The porous substrate is configured to provide the capillary action that draws the vaporizable material from the reservoir chamber 2006, 2106 towards the surface heater to be vaporized into aerosol by the surface heater. The aerosol is then combined with airflow 2020, 2120 traveling along an airflow passageway 2024, 2124 of the vaporizer device for inhalation by a user.

The reservoir systems 2000, 2100 also include an airflow restrictor 2018, 2118 that restricts the passage of airflow 2020, 2120 along the airflow passageway 2024, 2124 of the vaporizer device, such as when a user puffs on the vaporizer device. The restriction of airflow 2020, 2120 caused by the airflow restrictor 2018, 2118 can allow a vacuum to be formed along a part of the airflow passageway 2024, 2124 downstream from the airflow restrictor 2018, 2118. The vacuum created along the airflow passageway 2024, 2124 can assist with drawing aerosol along the airflow passageway 2024, 2124 for inhalation by a user. At least one airflow restrictor 2018, 2118 can be included in each of the reservoir systems 2000, 2100 and the airflow restrictor 2018, 2118 can include any number of features for restricting airflow along the airflow passageway 2024, 2124.

As shown in FIGS. 19 and 20, each of the reservoir systems 2000, 2100 can also include a vent 2010, 2110 that can be configured to selectively allow the passage of air into the reservoir chamber 2006, 2106 for increasing the pressure within the reservoir chamber 2006, 2106, such as to relieve the reservoir chamber 2006, 2106 from negative pressure (vacuum) resulting from the vaporizable material being drawn out of the reservoir chamber 2006, 2106, as discussed above. At least one vent 2010, 2110 can be associated with the reservoir chamber 2006, 2106. The vent 2010, 2110 can be an active or passive valve and the vent 2010, 2110 and can include any number of features for allowing air to pass into the reservoir chamber 2006, 2106 to relieve negative pressure created in the reservoir chamber 2006, 2106. Various embodiments of vents and vent configurations (e.g., embodiments of porous substrates including one or more vents) are described in greater detail below.

For example, as shown in FIG. 19, an embodiment of the vent 2010 can include a passageway that extends between the reservoir chamber 2006 and the airflow passageway 2024. In another example, as shown in FIG. 20, an embodiment of the vent 2110 can include a passageway that extends between the reservoir chamber 2106 and ambient air outside the system 2100. In either instance, the vent 2010, 2110 includes a diameter that is sized such that a fluid tension of the vaporizable material prevents the vaporizable material from passing through the passageway when the pressure is equalized across the vent 2010 (e.g., the pressure in the reservoir chamber 2006 is approximately the same as the pressure in the airflow passageway 2024 or the pressure in the reservoir chamber 2106 is approximately the same as the pressure outside of the system 2100). However, the diameter of the vent passageway can be sized such that a vacuum pressure created in the reservoir chamber 2006, 2106 disrupts the surface tension of the vaporizable material along the vent passageway.

Accordingly, with respect to FIG. 19, a volume of air may pass from the airflow passageway 2024 to the reservoir chamber 2006 and relieve the vacuum pressure. Similarly, with respect to FIG. 20, a volume of air may pass from outside of the system 2100 to the reservoir chamber 2106 and relieve the vacuum pressure. Once the volume of air is added to the reservoir chamber 2006, 2106 the pressure is again equalized across the vent 2010, 2110 thereby allowing the surface tension of the vaporizable material to prevent air from entering in the reservoir chamber 2006, 2106 as well as preventing the vaporizable material from leaking out of the reservoir chamber 2006, 2106 through the vent passageway. Additionally, the vent passageway can include a length that, in addition to the diameter, defines a volume of fluid that can be passed through the vent when a pressure differential is experienced across the vent.

In one example embodiment, dimensions of the vent passageway diameter can include approximately 0.3 mm to 0.6 mm, and can also include diameters having a dimension that approximately 0.1 mm to 2 mm. The material of the vent passageway can also assist with controlling the vent, such as determining a contact angle between the walls of the vent passageway and the vaporization material. The contact angle can have an effect on the surface tension created by the vaporization material and thus effects the threshold pressure differential that can be created across the vent before a volume of fluid is allowed to pass through the vent, such as described above. The vent passageway can include a variety of shapes/sizes and configurations that are within the scope of this disclosure. Additionally, various embodiments of cartridges and parts of cartridges that include one or more of a variety of venting features are described in greater detail below.

Positioning of the vent 2010, 2110 (e.g., a passive vent) and the airflow restrictor 2018, 2118 relative to atomizer 2004, 2104 assists with effective functioning of the reservoir systems 2000, 2100. For example, improper positioning of either the vent 2010, 2110 or the airflow restrictor 2018, 2118 can result in unwanted leaking of the vaporizable material from the reservoir chamber 2006, 2106. The present disclosure addresses effective positioning of the vent 2010, 2110 and airflow restrictor 2018, 2118 relative to the atomizer 2004, 2104 (containing the porous substrate). For example, a small or no pressure differential between a passive vent and the porous substrate can result in an effective reservoir system for relieving vacuum pressure in the reservoir chamber and resulting in effective capillary action of the porous substrate while preventing leaking. Configurations of the reservoir system having effective positioning of the vent and airflow restrictor relative to the atomizer is described in greater detail below.

As shown in FIG. 19, the airflow restrictor 2018 may be positioned upstream from the atomizer 2004 along the airflow passageway 2024 and the vent 2010 is positioned along the reservoir chamber 2006 such that it provides fluid communication between the reservoir chamber 2006 and a part of the airflow passageway 2024 that is downstream from the atomizer 2004. As such, when a user puffs on the vaporizer device, a negative pressure is created downstream from the airflow restrictor 2018 such that the atomizer experiences negative pressure. Similarly, a side of the vent 2010 in communication with the airflow passageway 2024 also experiences the negative pressure.

As such, a small to no amount of pressure differential is created between the vent 2010 and the atomizer 2004 during the puff (e.g., when the user draws in or sucks in air from the vaporizer device). However, after the puff the capillary action of the porous substrate will draw vaporizable material from the reservoir chamber 2006 to replenish the vaporizable material that was vaporized and inhaled as a result of the previous puff. As a result, a vacuum or negative pressure will be created in the reservoir chamber 2006. A pressure differential will then occur between the reservoir chamber 2006 and the airflow passageway 2024. As discussed above, the vent 2010 can be configured such that a pressure differential (e.g., a threshold pressure difference) between the reservoir chamber 2006 and the airflow passageway 2024 allows a volume of air to pass from the airflow passageway 2024 into the reservoir chamber 2006 thereby relieving the vacuum in the reservoir chamber 2006 and returning to an equalized pressure across the vent 2010 and a stable reservoir system 2000.

In another embodiment, as shown in FIG. 20, the airflow restrictor 2118 may be positioned downstream from the atomizer 2104 along the airflow passageway 2124 and the vent 2110 is positioned along the reservoir chamber 2106 such that it provides fluid communication between the reservoir chamber 2106 and a part of the airflow passageway 2124 that is upstream from the atomizer 2104. As such, when a user puffs on the vaporizer device, the atomizer 2104 and vent 2118 experience little to no suction or negative pressure as a result of the puff, thus resulting in little to no pressure differential between the atomizer 2104 and the vent 2110. Similar to the case in FIG. 19, the pressure differential created across the vent 2110 will be a result of the capillary action of the porous substrate drawing vaporizable material from the reservoir chamber 2106 after the puff. As a result, a vacuum or negative pressure will be created in the reservoir chamber 2106. A pressure differential will then occur across the vent 2110.

As discussed above, the vent 2010, 2110 can be configured such that a pressure differential (e.g., a threshold pressure difference) between the reservoir chamber 2006, 2106 and the airflow passageway 2024 or atmosphere (ambient air) allows a volume of air to pass into the reservoir thereby relieving the vacuum in the reservoir chamber 2006, 2106. This allows the pressure to be equalized across the vent 2010, 2110 and the reservoir system 1900, 2000 to be stabilized. The vent 2010, 2110 can include various configurations and features and can be positioned in a variety of positions along the cartridge, such as to achieve various results. For example, one or more vents can be positioned adjacent or forming a part of the atomizer. In such a configuration, the one or more vents can provide fluid (e.g., air) communication between the reservoir chamber and the atomizer (through which airflow passes through when a user puffs on the vaporizer and is thus part of the airflow pathway).

Similarly, as described above, a vent placed adjacent or forming a part of the atomizer can allow air to travel into the reservoir chamber via the vent to increase the pressure inside the reservoir chamber, thereby effectively relieving the vacuum pressure created as a result of the vaporizable material being drawn into the porous substrate of the atomizer. As such, relief of the vacuum pressure allows for continued efficient and effective capillary action of the vaporizable material into the atomizer via the porous substrate for creating inhalable vapor during subsequent puffs on the vaporizer device by a user.

In some aspects, the vaporizer cartridges described herein utilize an atomizer having a porous substrate that is configured to draw vaporizable material from a reservoir chamber, in which the porous substrate has at least one vent extending therethrough that can be configured to allow the passage of air into the reservoir chamber in response to the withdrawal of at least a portion of the vaporizable material from the reservoir chamber (e.g., while or after a user puffs on the cartridge). That is, the at least one vent can be configured to selectively allow the passage of air into the reservoir chamber for increasing the internal pressure within the reservoir chamber. This can relieve the reservoir chamber from negative pressure (vacuum) created from the vaporizable material being drawn out of the reservoir chamber and into the porous substrate. The atomizer also includes at least one surface heater that is configured to selectively heat at least a portion of the vaporizable material drawn into the porous substrate.

The porous substrate can have a variety of configurations. In general, the porous substrate extends from a first surface to a second surface that is opposite the first surface. In some aspects, the first surface can be positioned within the reservoir chamber, and therefore be in direct contact with vaporizable material disposed therein. In this way, at least a portion of the porous substrate resides within the reservoir chamber. The porous substrate can have any suitable shape and size. In one aspect, the porous substrate can have a substantially rectangular shape. The size and shape of the porous substrate can be dependent at least upon the structural dimensions of the other components of the cartridge and the cartridge itself. For example, in various aspects, the first and second surfaces may optionally be parallel or at least approximately parallel. In other aspects, the first and second surfaces may have other relative orientations. In certain aspects, one or both of the first and second surfaces may optionally be at least approximately planar. In certain aspects, either or both of the first and second surface may be curved, undulating, ridged, or otherwise be non-planar on at least some of the surface.

The porous substrate may be made of a porous ceramic material, a sintered material, other porous materials, such as high-temperature resistant materials including, for example and without limitation, metals, glass, silicon, carbon or high-temperature resistant plastic materials such as, for example and not limitation, polyphenylene sulfide (PPS), liquid crystal polymer (LCP), or polyether ether ketone (PEEK). The porous substrate may be characterized by having a plurality of voids or spaces, allowing for the absorption and transport of the vaporizable material from the reservoir chamber. The void size, particle size, or porosity of the porous substrate may be chosen based on various factors, for example to achieve desired characteristics or due to specific parameters of the cartridge/device (such as, for example, the viscosity of the vaporizable material and/or other design considerations). The plurality of voids or spaces may be an inherent property of the material (or materials) or may be formed from, for example, drilled (e.g., laser drilled) holes. The porous substrate may be further characterized by having a rigid, non-deformable structure.

The at least one vent may have a variety of configurations. In some aspects, the at least one vent may have a varying cross-sectional area, whereas in other aspects, the at least one vent may have a constant cross-sectional area. For example, the at least one vent may have a first portion with a first cross-sectional area and a second portion with a second cross-sectional area that is less than the first cross-sectional area. In some aspects, the first portion can be adjacent to the reservoir chamber and the second portion can be distal to the reservoir chamber. (may want to say they can be both proximate to reservoir chamber) As a result, the cross-sectional area can allow for lower pressure at the interface between the vaporizable material and the influx of air into the reservoir chamber, whereas the second cross-sectional area can allow for higher pressure within a portion of the vent passageway to inhibit vaporizable material from passing therethrough, and thus leaking from the reservoir chamber.

By having different cross-sectional areas, this can allow for lower air bubble pinch off resistance on a first end of the first portion of the at least one vent that is in contact with the reservoir chamber and higher capillary pressure on a second end of the second portion of the at least one vent, which is opposite the first end, to offset any static head of vaporizable material in the reservoir chamber. In some aspects, the at least one vent can have a conical shape, whereas in other aspects, the at least one vent can have any other possible shape.

The first portion can extend inward from the first surface of the porous substrate and the second portion can extend inward from the second surface of the porous substrate. In other aspects, the at least one vent can be positioned at the edge or end of the porous substrate in which the at least one vent is partially bounded by an internal surface of the reservoir housing. A person skilled in the art will appreciate that the at least one vent can be positioned at various locations along the length of the porous substrate (e.g., at an edge or end, in the middle, or any other possible location therebetween). In some aspects, the at least one vent can have a conical shape, whereas in other aspects, the at least one vent can have any other possible shape.

The at least one surface heater may include one or more electrically conductive layers on or in contact with at least a portion of the porous substrate. In some examples, the one or more electrically conductive layers may include a trace pattern deposited on a surface (e.g., the second surface) or at least a portion of a surface (e.g., the second surface) of the porous substrate. A trace pattern may be configured to achieve a desired and controlled electrical resistance, and may or may not be uniform in thickness or extent along the surface of the porous substrate. Specific shapes, patterns, thickness, etc. of the surface heater may be advantageous in allowing control of heat delivery to the porous substrate to be controlled and allowing for the vaporizable material from the reservoir chamber to pass through. Alternatively, the electrically conductive layer may be a plate or other continuous layer that covers the entire surface or a portion of the second surface of the substrate. Such a plate or other continuous layer may include features such as holes, microperforations, etc. for allowing vaporizable material from the reservoir chamber to pass through the surface heater. The electrically conductive layer may be made from any electrically conductive material, such as, for example and without limitation, a nickel chromium alloy, stainless steel, nickel, platinum, gold, copper, or aluminum. The electrically conductive layer may be a micro-electrical-mechanical systems (MEMS) layer. In this manner, or in other approaches consistent with the current subject matter, a surface heater can be in contact with at least a portion of a surface (e.g., the second surface) of the porous substrate.

The at least one surface heater may be adhered to the porous substrate in a number of ways, such as by pulsed laser deposition, physical vapor deposition, chemical vapor deposition, electroplating, electro-less plating, screen printing, or the like. In some variations of the current subject matter, the at least one surface heater may be a stamped part that is snapped onto or otherwise mechanically retained by the porous substrate. In other variations, the at least one surface heater may be a stamped part that is insert molded into the porous substrate. In other variations, the at least one surface heater is fixed to the porous substrate by any secure attachment method.

The at least one surface heater may have areas of lower electrical resistance that can be used as contacts (electrical contacts) for electrically interfacing the cartridge with a vaporizer body. The electrical contact areas may be positioned on the second surface of the porous substrate, while in some variations the electrical contact areas may be on a different surface of the porous substrate.

Figure 21:
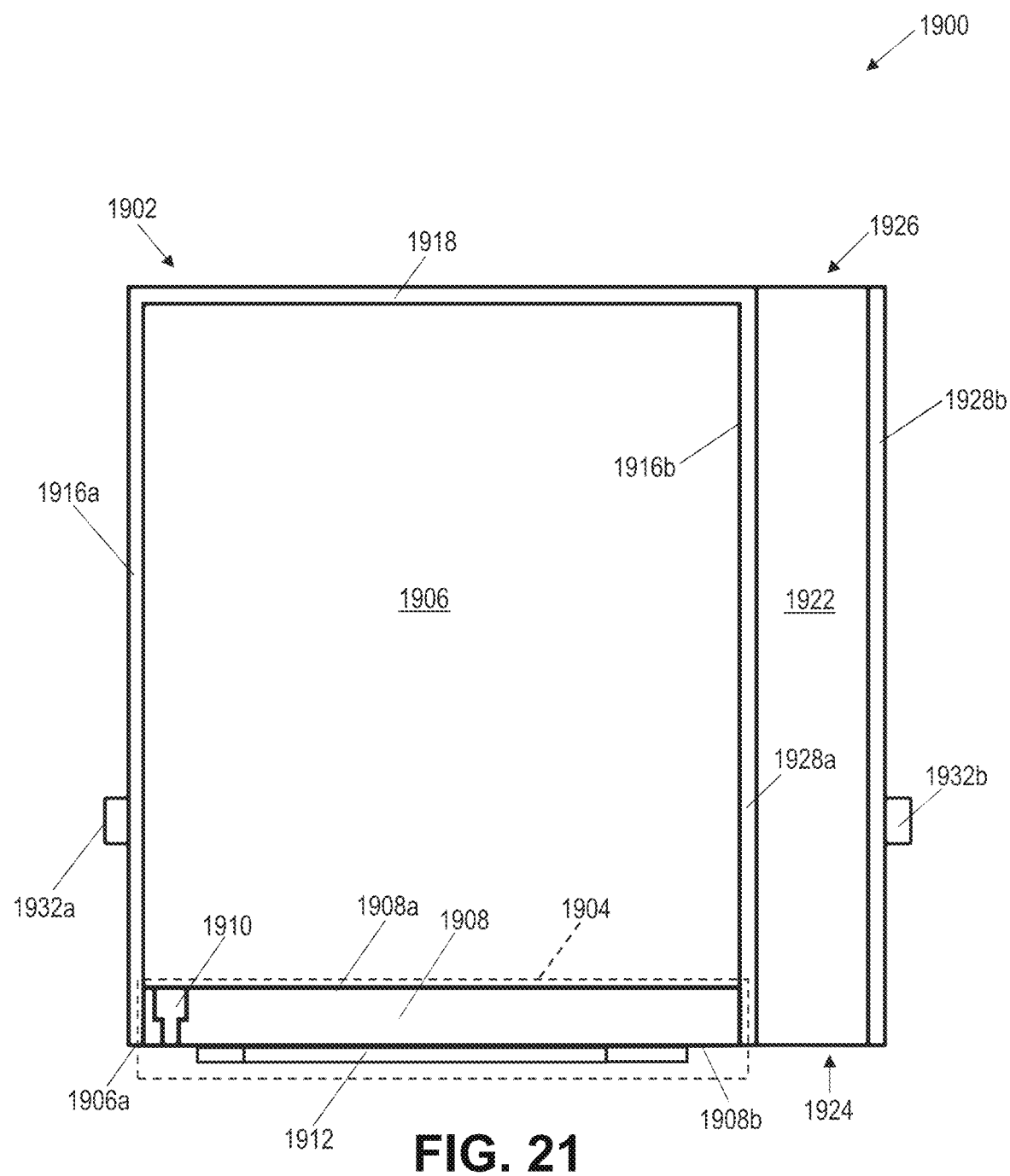
FIG. 21 is a cross-sectional front view of another exemplary embodiment of a cartridge for use in a vaporizer device consistent with implementations of the current subject matter, the cartridge having a reservoir and an atomizer that includes a porous substrate having at least one vent extending therethrough and at least one surface heater.
Figure 22:
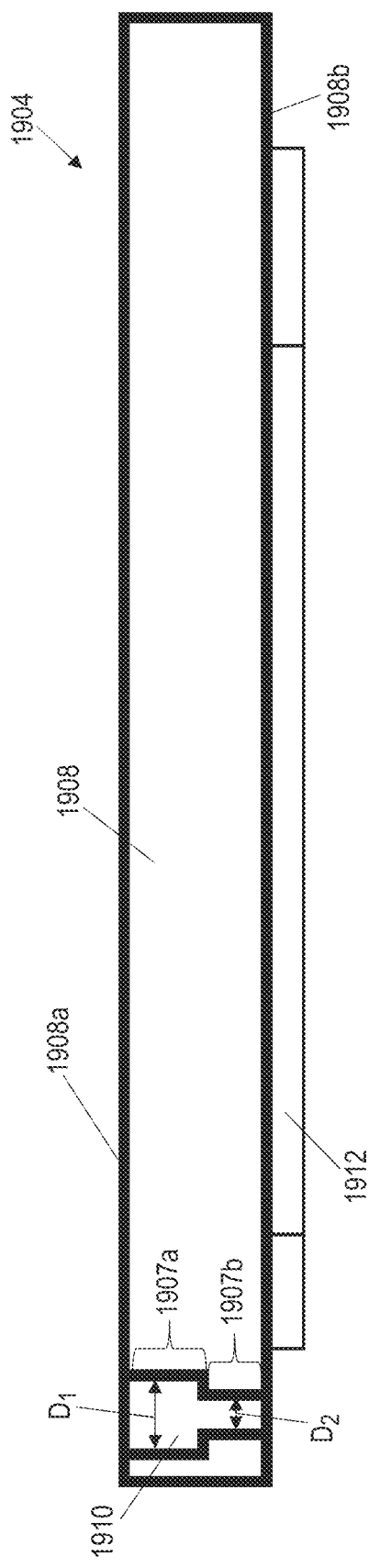
FIG. 22 is a magnified cross-sectional view of the atomizer of FIG. 21.

FIG. 21 illustrates an exemplary cartridge 1900 for a vaporizer device. More specifically, the cartridge 1900 includes a reservoir housing 1902 and an atomizer 1904 that is in fluid communication with a reservoir chamber 1906. The atomizer 1904, as shown in FIGS. 21 and 22, includes a porous substrate 1908 having at least one vent 1910 extending therethrough, and a surface heater 1912. For purposes of simplicity only, certain components of the cartridge 1900 are not illustrated.

The reservoir housing 1902 includes the reservoir chamber 1906. The reservoir chamber 1906 is configured to hold a vaporizable material (not shown). While the reservoir housing 1402 can have a variety of sizes and shapes, the reservoir housing 1902, as shown in FIG. 21, is substantially rectangularly shaped. The reservoir housing 1902 includes a first and second opposing sidewalls 1916a, 1916b and a top wall 1918 that extends therebetween. As shown, these walls 1916a, 1916b, 1918 define at least a portion of the reservoir chamber 1906.

Figure 23:
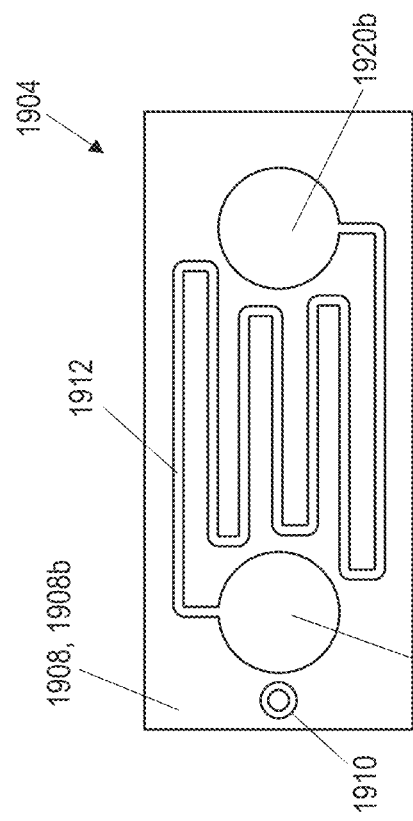
FIG. 23 is a magnified bottom view of the atomizer of FIG. 22.

While the porous substrate 1908 can have a variety of configurations, the porous substrate 1908, as shown in FIGS. 21-23, is substantially rectangularly shaped. The porous substrate 1908 extends from a first surface 1908a to a second, opposing surface 1908b. In this illustrated embodiment, the porous substrate 1908 at least partially resides within the reservoir chamber 1906. In particular, the first surface 1908a is positioned within the reservoir chamber 1906 and the second surface 1908b is flush with and defines a portion of the distal end 1906a of the reservoir housing 1902. As a result, the first surface 1908a can be in direct contact with vaporizable material disposed within the reservoir chamber 1906. In other embodiments, the second surface 1908b can be positioned distal to the distal end 1906a of the reservoir housing 1902. Further, as shown in FIG. 21, the first surface 1908a defines a portion of the reservoir chamber 1906. In use, when the reservoir chamber 1906 is filled with vaporizable material, the vaporizable material is drawn into the porous substrate 1908 through the first surface 1908a towards the second surface 1908b for vaporization.

As further shown in FIGS. 21-23, the at least one vent 1910 extends from the first surface 1908a to the second surface 1908b of the porous substrate 1908. As discussed above, the at least one vent 1910 is configured to allow the passage of air into the reservoir chamber 1906 in response to the withdrawal of at least a portion of the vaporizable material from the reservoir chamber 1906 (e.g., while or after a user puffs on the cartridge 1900 during use). As a result, the internal pressure of the reservoir chamber 1906 can be equalized, and therefore substantially prevent a vacuum from being created within the reservoir chamber 1906, which can inhibit withdrawal of the vaporizable material therefrom. While the at least one vent 1910 can have a variety of configurations, in this illustrated embodiment, the at least one vent includes a first portion 1907a with a first diameter ($D_1$) and a second portion 1907b with a second diameter ($D_2$) that is less than the first diameter. As such, the cross-sectional area of the first portion 1907a is greater than the cross-sectional area of the second portion 1907b. As shown, the first portion 1907a extends inward from the first surface 1908a of the porous substrate 1908 and the second portion 1907b extends inward from the second surface 1908b of the porous substrate 1908.

While the surface heater 1912 can have a variety of configurations, as shown in FIG. 21, and in more detail in FIGS. 22 and 23, the surface heater 1912 includes an electrically conductive layer having a trace pattern. The surface heater 1912 is deposited on a portion of the second surface 1908b of the porous substrate 1908. Further, as shown, two electrical contacts 1920a, 1920b are positioned at opposite ends of the trace pattern of the electrical conductive layer. Each of the electrical contacts 1920a, 1920b are sized and shaped for connection with contact pins (e.g., pogo pins or leaf spring pins) of a vaporizer body, like vaporizer body 2102 shown in FIGS. 24 and 25, for operation. In use, the surface heater 1912 is activated to generate heat so as to vaporize at least a portion of the vaporizable material that is within the porous substrate 1908 into vaporized vaporizable material.

As further shown in FIG. 21, the cartridge 1900 also includes an internal channel 1922 that extends from an inlet 1924 to an outlet 1926 of the cartridge 1900. The internal channel 1922 is configured to direct air and vaporized vaporizable material through the cartridge 1900 for inhalation by a user. While the internal channel 1922 can have a variety of configurations, in this illustrated embodiment, the internal channel 1922 is defined by first and second opposing sidewalls 1928a, 1928b. In this illustrated embodiment, the sidewall 1916b of the reservoir housing 1902 and the first sidewall 1928a of the internal channel 1922 are the same. In other embodiments, the internal channel 1922 can be sized and shaped differently, including any other possible shape.

Figure 24:
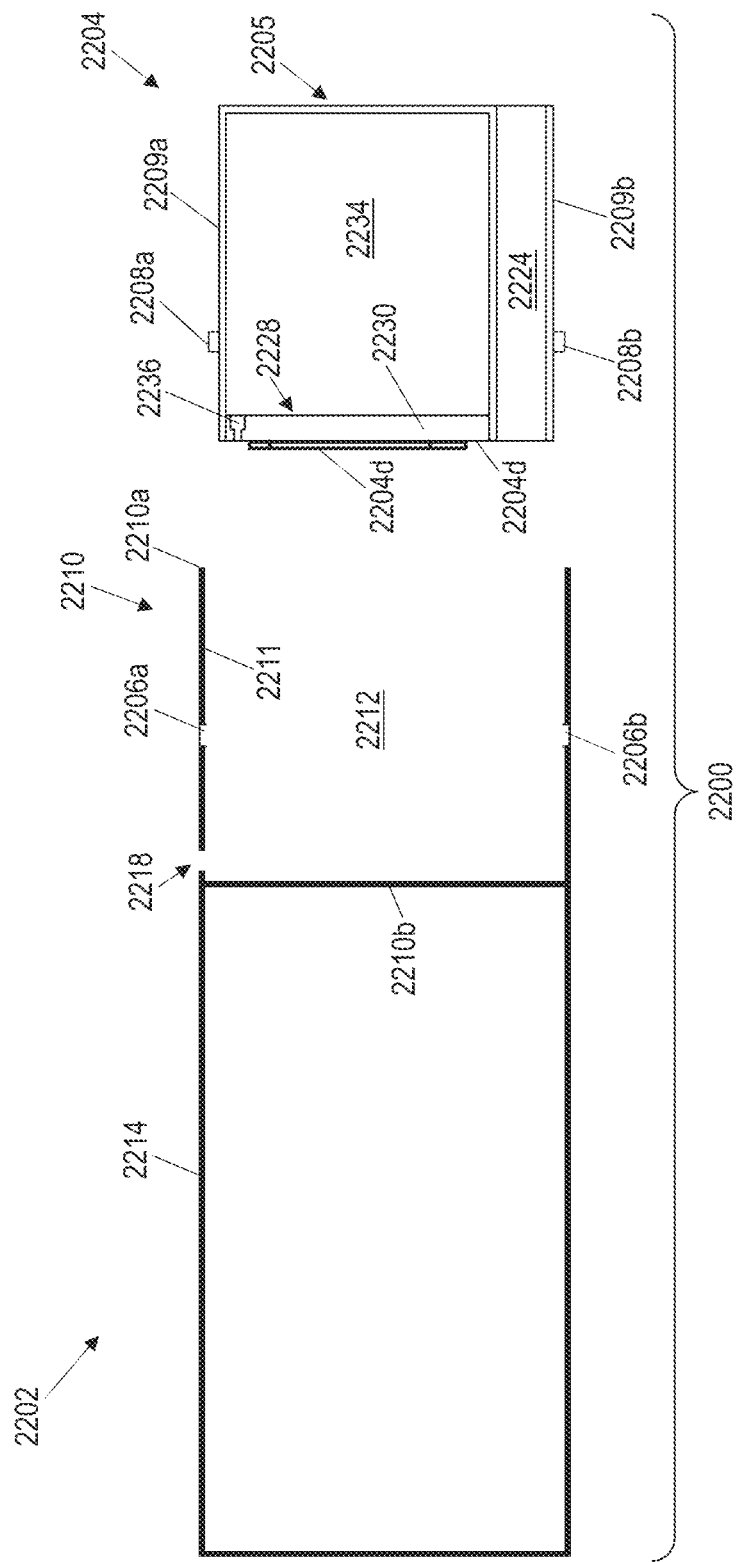
FIG. 24 is a partially transparent top view of another exemplary embodiment of an exemplary embodiment of a vaporizer device that includes a vaporizer body and a cartridge having a reservoir chamber and an atomizer consistent with implementations of the current subject matter, showing the vaporizer body and cartridge separated from each other.
Figure 25:
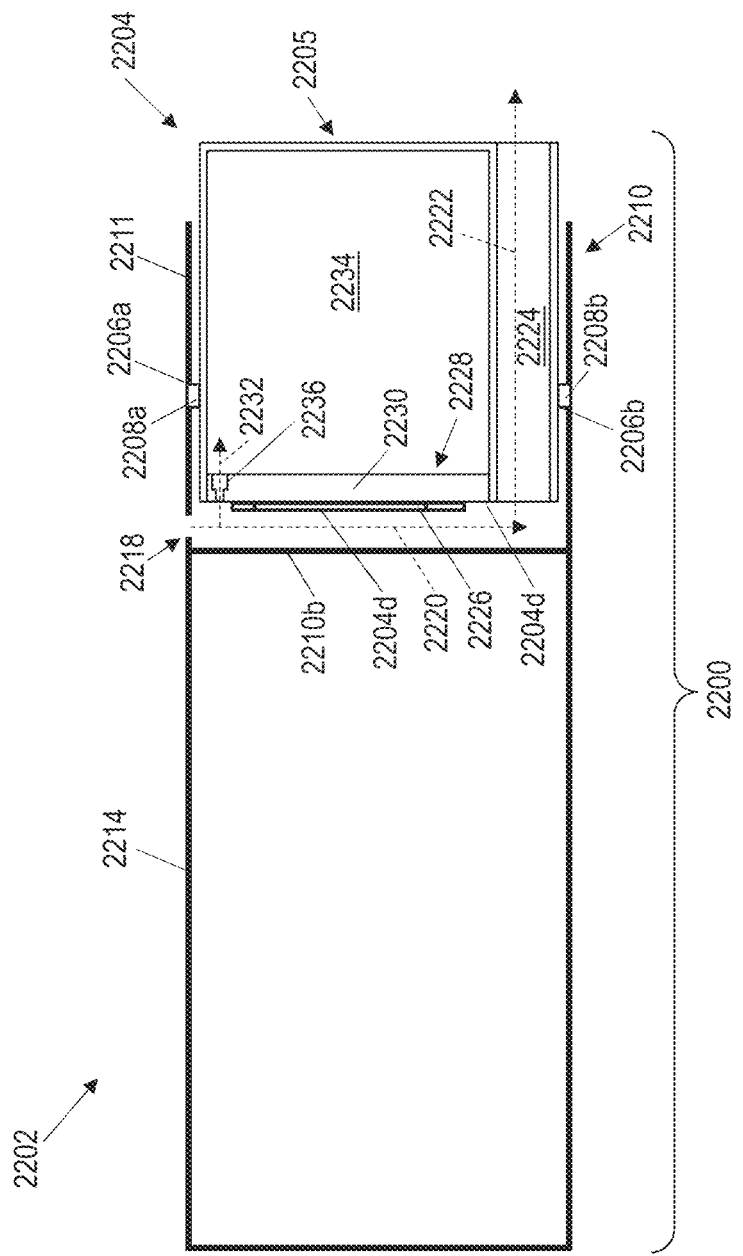
FIG. 25 is a partially transparent top view of the vaporizer device of FIG. 24, showing the cartridge inserted into a cartridge receptacle of the vaporizer body.

Further, as shown in FIG. 21, the cartridge 1400 also includes a set of coupling elements 1932a, 1932b that can be used to selectively couple the cartridge 1900 to a vaporizer body, such as vaporizer body 2102 in FIGS. 24 and 25. While the first set of coupling elements 1932a, 1932b can have a variety of configurations, in this illustrated embodiment, each coupling element 1932a, 1932b includes a protrusion that extends outwardly from a sidewall of the cartridge 1900. In particular, the protrusion of the first coupling element 1932a extends from the first sidewall 1916a of the reservoir housing 1902 and the protrusion of the second coupling element 1932b extends from the second sidewall 1928b of the internal channel 1922 of the cartridge 1900.

FIGS. 24 and 25 illustrate an exemplary vaporizer device 2200 that includes a vaporizer body 2202 and a cartridge 2204. In FIG. 24, the vaporizer body 2202 and the cartridge 2204 are illustrated in a decoupled configuration, whereas in FIG. 25, the vaporizer body 2202 and the cartridge 2204 are illustrated in a coupled configuration. The cartridge 2204 is similar to cartridge 1900 in FIG. 21 and is therefore not described in detail herein. For purposes of simplicity, certain components of the vaporizer device 2200 are not illustrated in FIGS. 24 and 25.

The vaporizer body 2202 and the cartridge 2204 can be coupled to each other by way of corresponding coupling elements. For example, as shown in FIGS. 24 and 25, the vaporizer body 2202 includes a first set of coupling elements 2206a, 2206b, and the cartridge 2204 includes a second set of corresponding coupling elements 2208a, 2208b. While the first and second set of coupling elements can have a variety of configurations, in this illustrated embodiment, the first set of coupling elements 2206a, 2206b include two recess pores extending inward into the vaporizer body 2202 and the second set of coupling elements 2208a, 2208b include two protrusions extending outwardly from two opposing sidewalls 2209a, 2209b of the cartridge 2204. In other embodiments, the first and second set of coupling elements 2206a, 2206b, 2208a, 2208b, can have any other suitable corresponding configuration (e.g., protrusions, channels, troughs, holes, hooks, grooves, detents, etc.) that can be used to selectively couple the cartridge 2204 to the vaporizer body 2202.

The vaporizer body 2202 can have a variety of configurations. As shown in FIGS. 24 and 25, the vaporizer body 2202 includes a sleeve 2210 that extends from a proximal end 2210a to a distal end 2210b. The sleeve 2210 defines a cartridge receptacle 2212 within the vaporizer body 2202 that is configured to receive at least a portion of the cartridge 2204. The distal end 2210b of the sleeve 2210 is coupled to a chassis 2214 that is configured to house at least a portion of additional components of the vaporizer device 2200, such as, for example, a power source, input device(s), sensor(s), output, a controller, communication hardware, memory, and the like. Once the cartridge 2204 is coupled to the vaporizer body 2202, a first airflow path 2220, as shown in FIG. 25, is created within the cartridge receptacle 2212 between the distal end 2210b of the sleeve 2210 and a distal end 2204d of the cartridge 2204.

Further, as shown in FIGS. 24 and 25, a first air inlet 2218 extends through a wall 2211 of the sleeve 2210. This first air inlet 2218 is configured to allow at least a portion of ambient air outside of the vaporizer body 2202, and thus outside of the reservoir housing 2205 of the cartridge 2204, to enter the vaporizer device 2200. In use, when a user puffs on the device, at least a portion of ambient air enters the vaporizer body 2202 and travels through the first airflow path 2220. As described in more detail below, vaporized vaporizable material joins the first airflow path 2220 and combines with at least a portion of the air to form a mixture. The mixture travels through the remaining portion of the first airflow path 2220 and then through a second airflow path 2222 that extends through an internal channel 2224 of the cartridge 2204. As such, the first and second airflow paths 2220, 2222 are in fluid communication with each other.

In use, once the cartridge 2204 is coupled to the vaporizer body 2202, the surface heater 2226 of the atomizer 2228 can be activated by a user puffing on the cartridge 2204 and at least a portion of vaporizable material within the porous substrate 2230 of the atomizer 2228 is vaporized into vaporized vaporizable material. This puffing also concurrently draws ambient air into the first airflow path through the first air inlet 2218 of the sleeve 2210. As a result, at least a portion of the vaporized vaporizable material joins the air traveling along the first airflow path 2220. Subsequently, at least a portion of the joined vaporized vaporizable material and air continues to travel through the vaporizer body 2202 and into the second airflow path 2222 of the cartridge 2204. As the joined vaporized vaporizable material and air travel through at least the second airflow path 2222, and thus, the internal channel 2224 of the cartridge 2204, they at least partially condense into aerosol for subsequent inhalation by a user.

Further, during puffing, at least a portion of ambient air 2232 that is drawn through the first air inlet 2218 of the sleeve 2210 enters into the reservoir chamber 2234 of the cartridge 2204 through the at least one vent 2236 of the porous substrate 2230 of the atomizer 2228. As a result, the negative pressure that is created within the reservoir chamber 2234 as the vaporizable material is drawn therefrom can be reduced. That is, the influx of ambient air 2232 into the reservoir chamber 2234 replaces at least a portion of the volume of the vaporizable material being withdrawn therefrom. As a result, the internal pressure of the reservoir chamber 2234 of the cartridge 2204 can at least be partially equalized.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for a vaporizer device, the cartridge comprising:
   a reservoir housing including a reservoir chamber configured to selectively hold a vaporizable material; and
   an atomizer in fluid communication with the reservoir chamber, the atomizer comprising,
      a porous substrate configured to draw the vaporizable material from the reservoir chamber, the porous substrate comprising at least one vent extending therethrough, the at least one vent being configured to allow the passage of air into the reservoir chamber in response to the withdrawal of at least a portion of the vaporizable material from the reservoir chamber, and
      at least one surface heater configured to heat at least a portion of vaporizable material drawn into the porous substrate into a vaporized vaporizable material, the at least one surface heater comprising at least one electrically conductive layer deposited on a portion of the porous substrate;
   wherein the at least one vent has a first portion with a first cross-sectional area and a second portion with a second cross-sectional area that is less than the first cross-sectional area, and wherein the first portion is adjacent to the reservoir chamber and the second portion is distal to the reservoir chamber.

2. The cartridge of claim 1, wherein the porous substrate extends from a first surface to a second surface that is opposite the first surface, and wherein at least the first surface is positioned within the reservoir chamber and the at least one electrically conductive layer is deposited on the second surface.

3. A vaporizer device, comprising:
a vaporizer body that includes a first airflow path; and
the cartridge of claim 1 that is selectively coupled to the vaporizer body, wherein at least a portion of the atomizer is exposed to the first airflow path and the at least one vent is in fluid communication with the first airflow path.

4. The vaporizer device of claim 3, wherein the cartridge includes a second airflow path that is in fluid communication with the first airflow path.

5. A cartridge for a vaporizer device, the cartridge comprising:
a reservoir housing including a reservoir chamber configured to selectively hold a vaporizable material; and
an atomizer in fluid communication with the reservoir chamber, the atomizer comprising,
a substrate having a channel extending at least partially therethrough and a plurality of voids, the channel being configured to receive a predetermined volume of vaporizable material from the reservoir chamber at a predetermined rate, the plurality of voids being configured to draw the vaporizable material present within the channel, and
at least one surface heater that is configured to selectively heat at least a portion of the vaporizable material drawn into the plurality of voids from the channel into a vaporized vaporizable material.

6. The cartridge of claim 5, wherein the at least one surface heater comprises at least one electrically conductive layer deposited on a portion of the substrate.

7. The cartridge of claim 5, wherein the at least one surface heater comprises a first surface heater positioned on a first portion of the substrate, and a second surface heater positioned on a second portion of the substrate.

8. The cartridge of claim 5, wherein the substrate has at least two spaced apart surfaces that each define a boundary of the channel.

9. The cartridge of claim 8, wherein the substrate includes a base that extends between the at least two spaced apart surfaces, and wherein the base further defines the boundary of the channel.

10. The cartridge of claim 9, wherein the substrate is formed as a unitary structure.

11. The cartridge of claim 5, wherein the substrate includes first and second sidewalls that are spaced apart from one another in a first direction, and wherein the first and second sidewalls each extend from an inner surface to an outer surface, each inner surface defining a boundary of the channel.

12. The cartridge of claim 11, wherein the substrate includes third and fourth sidewalls that are spaced apart from one another in a second direction that is opposite the first direction, and wherein the third and fourth sidewalls each extend from an inner surface to an outer surface, each inner surface defining a boundary of the channel.

13. The cartridge of claim 5, wherein the substrate includes at least one vent extending from a first surface of the substrate to a second surface of the substrate, the second surface being opposite of the first surface.

14. The cartridge of claim 13, wherein the at least one vent has a first portion with a first cross-sectional area and a second portion with a second cross-sectional area that is less than the first cross-sectional area.

15. The cartridge of claim 14, wherein the first portion is adjacent to the reservoir chamber and the second portion is distal to the reservoir chamber.

16. A vaporizer device, comprising:
a vaporizer body that includes a first airflow path; and
the cartridge of claim 5 that is selectively coupled to the vaporizer body, wherein at least a portion of the atomizer is exposed to the first airflow path.

17. The vaporizer device of claim 16, wherein the cartridge includes a second airflow path that is in fluid communication with the first airflow path.

* * * * *